US006890484B2

(12) United States Patent
Bautista et al.

(10) Patent No.: US 6,890,484 B2
(45) Date of Patent: May 10, 2005

(54) IN LINE TEST DEVICE AND METHODS OF USE

(75) Inventors: Lorraine Bautista, San Diego, CA (US); Zhumin Guan, Hangzhou (CN)

(73) Assignee: Acon Laboratories, Inc., San Diego, CA (US)

( * ) Notice: Subject to any disclaimer, the term of this patent is extended or adjusted under 35 U.S.C. 154(b) by 291 days.

(21) Appl. No.: 10/278,686

(22) Filed: Oct. 22, 2002

(65) Prior Publication Data

US 2003/0129767 A1 Jul. 10, 2003

Related U.S. Application Data

(63) Continuation-in-part of application No. 09/860,408, filed on May 18, 2001, now Pat. No. 6,565,808, which is a continuation-in-part of application No. PCT/US02/13566, filed on Apr. 29, 2002.

(51) Int. Cl.[7] .................................................. G01N 33/48

(52) U.S. Cl. .......................... 422/58; 422/100; 422/102; 422/103; 436/165; 435/288.2

(58) Field of Search ............................ 422/58, 61, 100, 422/102, 103; 436/165, 172; 435/288.2

(56) References Cited

U.S. PATENT DOCUMENTS

| | | | |
|---|---|---|---|
| 4,275,149 | A | 6/1981 | Litman et al. |
| 4,299,916 | A | 11/1981 | Litman et al. |
| 4,635,488 | A | 1/1987 | Kremer |
| 4,707,450 | A | 11/1987 | Nason |
| 4,770,853 | A | 9/1988 | Bernstein |
| 4,803,048 | A | 2/1989 | Nason |
| 4,943,522 | A | 7/1990 | Eisinger et al. |
| 4,978,504 | A | 12/1990 | Nason |
| 5,084,245 | A | 1/1992 | Berke et al. |
| RE33,850 | E | 3/1992 | Snyder et al. |
| 5,250,412 | A | 10/1993 | Giegel |
| 5,260,221 | A | 11/1993 | Ramel et al. |
| 5,266,266 | A | 11/1993 | Nason |

(Continued)

FOREIGN PATENT DOCUMENTS

| | | |
|---|---|---|
| WO | WO 88/04431 | 6/1988 |
| WO | WO 97/23596 | 7/1997 |
| WO | WO 99/53291 | 10/1999 |
| WO | WO 00/54024 | 9/2000 |
| WO | WO 01/02854 | 1/2001 |
| WO | WO 02/04942 | 1/2002 |
| WO | WO 02/076373 | 10/2002 |

*Primary Examiner*—Lyle A. Alexander
(74) *Attorney, Agent, or Firm*—Foley & Lardner LLP

(57) ABSTRACT

The present invention recognizes that it can be desirable to have a sample receiving chamber integral to or engageable with a test platform, such as a test platform that includes a test strip. The sample receiving chamber is preferably separate or separable from the test platform, but that need not be the case. Preferably, a fluid flow actuating device or structure, such as a valve separates the sample receiving chamber from the test platform. The present invention provides such a device and methods of use. A first aspect of the present invention is a test device that includes a sample receiving chamber and a test platform that preferably includes a test element. The sample receiving chamber preferably engages the test platform and is optionally separable therefrom. A second aspect of the present invention is a method of detecting an analyte in a sample, including: providing a sample, contacting the sample with a test device and detecting the analyte in the sample. The test device preferably includes a sample receiving chamber and a test platform that includes a test element. Preferably, the sample receiving chamber engages the test platform and optionally the sample receiving chamber is separable from the test platform.

47 Claims, 13 Drawing Sheets

U.S. PATENT DOCUMENTS

| | | | | | |
|---|---|---|---|---|---|
| 5,415,994 | A | | 5/1995 | Imrich et al. | |
| 5,656,503 | A | | 8/1997 | May et al. | |
| 5,658,531 | A | | 8/1997 | Cope et al. | |
| 5,869,003 | A | | 2/1999 | Nason | |
| 5,877,028 | A | | 3/1999 | Chandler et al. | |
| 5,879,635 | A | | 3/1999 | Nason | |
| 5,965,453 | A | * | 10/1999 | Skiffington et al. | 436/165 |
| 5,965,456 | A | | 10/1999 | Malmqvist et al. | |
| 6,046,058 | A | | 4/2000 | Sun | |
| 6,074,606 | A | * | 6/2000 | Sayles | 422/58 |
| 6,156,025 | A | | 12/2000 | Niedospial, Jr. et al. | |
| 6,271,046 | B1 | | 8/2001 | Chandler | |
| 6,316,205 | B1 | | 11/2001 | Guan et al. | |
| 6,372,516 | B1 | | 4/2002 | Sun | |
| 6,375,896 | B1 | | 4/2002 | Wuske et al. | |
| 2001/0004532 | A1 | | 6/2001 | Chandler | |
| 2001/0023076 | A1 | | 9/2001 | Guan et al. | |
| 2001/0036645 | A1 | | 11/2001 | McNeirney et al. | |
| 2002/0009389 | A1 | | 1/2002 | Lappe et al. | |
| 2002/0009390 | A1 | | 1/2002 | Lappe et al. | |
| 2002/0027142 | A1 | | 3/2002 | Klein | |
| 2002/0052050 | A1 | | 5/2002 | Douglas et al. | |
| 2002/0054827 | A1 | | 5/2002 | Patel et al. | |
| 2002/0081233 | A1 | | 6/2002 | Lappe et al. | |
| 2002/0106809 | A1 | | 8/2002 | Cesarczyk | |

* cited by examiner

A

B

C

A

B

IN LINE TEST DEVICE AND METHODS OF USE

This application is a C-I-P of U.S. Utility application Ser. No. 09/860,408, filed May 18, 2001, now U.S. Pat. No. 6,565,808 entitled "In Line Test Device and Methods of Use" and a C-I-P of PCT/US02/13566, filed Apr. 29, 2002 which are incorporated by reference herein.

TECHNICAL FIELD

The present invention relates generally to the fields of test devices that include a sample receiving chamber and a test platform and methods of use thereof. Preferably, the sample receiving chamber can be used to extract, prepare or dilute a sample for analysis, such as using the test platform. The test platform can include a test element, such as a test strip. The test strip can be for an analyte of interest, such as an analyte relating to a disease state, medical condition or etiological agent. The present application incorporates by reference in their entirety the following applications or patents: non-provisional applications Ser. No. 09/579,673 filed May 26, 2000, Ser. No. 09/579,672 filed May 26, 2000now abandoned, Ser. No. 09/653,032 filed Sep. 1, 2000, now abandoned, and design patent application 29/133,183 filed Nov. 21, 2000.

BACKGROUND

A variety of sample collection and extraction test devices for clinical or home use are available and described in the literature. These test devices can utilize one of a variety of collection instruments to obtain and transfer a sample to a receptacle. The sample can be extracted from the collection device and diluted or mixed with one or more reagents in the receptacle. The sample can then be conveyed to a test element in order to determine the presence or absence of a substance, such as analyte detection. These devices can be used for an assortment of purposes, including the detection of drugs or biological compounds such as glucose or hormones, antibodies or etiological agents. Many of these devices are inefficient in sample extraction from the collection device. Also, many of these devices are complex in design and manufacture and fabricated of relatively expensive materials. The present invention addresses these problems, and provides related benefits.

BRIEF DESCRIPTION OF THE DRAWINGS

FIG. 3A depicts a cross section view along axis A—A of a test platform 2 of the present invention housing a test element, in this instance a single strip immunochromatographic test strip 3. The cross-section of an aperture 22 and opening 10, through which the detection and control zones of the immunochromatographic test strip 3 can be observed, are depicted. FIG. 3B depicts a test strip 3 comprised of multiple regions, in this instance having overlapping regions in order to be in fluid communication when a fluid is traveling via capillary flow. The test strip is made up of an application zone 30 in fluid communication with an optional second strip 31 with reagent zone 32. The second region 31 is in turn optionally in communication with a third region 33 with a sample detection zone 9 and optional control zone 11, overlapped by a fourth region 34 that promotes wicking of fluid through the test strip. FIG. 3C depicts a test strip 3 comprised of multiple regions, in this instance having regions end-to-end or overlapping in order to be in fluid communication when a fluid is traveling via capillary flow along the test strip. The test strip is made up of an application zone 30 with a downstream region optionally having label 32. A second strip 33 with a detection zone 9 and optional control zone 11 is adjacent to, and in fluid communication with the first region 30. And a third region 34 that promotes wicking of fluid through the test strip overlaps the second region 33.

FIG. 4A depicts a twist valve 40 such that openings of the valve do not aligned 41 and the valve is closed. Optionally the valve can be rotated such that openings align 42 and the valve is in the open position. Any intermediate alignment between the openings can be used as a way to regulate flow. FIG. 4B depicts a thin membrane and puncturing mechanism where a puncturable membrane 43 retains contents at the distal and of a sample receiving chamber and optionally a puncturing device 44 can come into contact with the puncturable membrane to rupture the membrane 45. FIG. 4C depicts a slide valve where an opening at the distal end of the sample receiving chamber is covered by a slide 46 to close the outlet 47 and when slid into a second position the opening is uncovered and provides an outlet 48 for the contents. FIG. 4D depicts a stopcock mechanism where the stopcock 49 can be rotated such that an outlet 50 is provided for the contents of the sample receiving chamber.

FIG. 6A depicts a front view, and FIG. 6B depicts a side view, of a male insert 60 of the sample receiving chamber 1. A grooved ridge 61 encircles the opening or proximal end 6 of the male insert 60. A stud 63 protrudes from, and an opening or outlet port 64 are positioned on the side wall of a cylindrical shaft 62 of the male insert 60. The outlet port 64 is flanked, above and below, by O-rings 65 that encircle the cylindrical shaft 62 of the male insert 60. FIG. 6C depicts a front view, and FIG. 6D depicts a side view, of a female receptor 66 of the sample receiving chamber 1. The female receptor 66 has a base 67 with a notch 68 for proper placement onto a test device of the present invention. An open groove guide 69 is situated along the side of the female receptor 66. FIG. 6E depicts the sample receiving chamber 1 in the closed position. The male insert 60 is coupled to the female receptor 66 such that the stud 63 sits near the top of the of the groove guide 69 and the outlet port 64 faces the inner wall of the female receptor 66 such that fluid cannot exit the sample receiving chamber 1. FIG. 6F depicts a sample receiving chamber 1 in the open position where upon rotation of the male insert 60, the groove guide 69 conveys the stud 63, and therefore the male insert 60, downward such that the outlet port 64 is below the inner wall of the female receptor 66.

FIG. 7A depicts a key 71 of a sample receiving chamber 1 that has a single orientation whereas FIG. 7B depicts a key 71 with a wide variety of orientations, essentially infinite due to the circular structure of the key 71. FIG. 7C depicts a key 71 with a sample receiving chamber 1 that can have between one and five orientations, whereas the key 71 and sample receiving chamber 1 of FIG. 7D can have between one and four orientations, the key 71 of a sample receiving chamber 1 in FIG. 7E can have between one and seven orientations, and the key 71 and sample receiving chamber 1 of FIG. 7F can have between one and three orientations. As set forth in FIG. 7D the key 71 can include a plurality of sample receiving chambers 1 which can include a sample or can be left unloaded with sample. As set forth in FIG. 7F, the key 71 can be color coded, for example blue (left side) and red (right side) of the upper figure. Such color coding can match color coding or other coding presented on a second device such that the sample receiving chamber 1 is properly aligned with the second device. Such orientation coding can also be accomplished as set forth in FIG. 7G, where the key 71 has structure such that it can engage a test platform in one orientation such that the sample receiving chamber 1 is aligned with a predetermined location. This aspect of the present invention is preferable when more than one sample receiving chamber 1 of the present invention is used to engage a test platform, such as a device that can collect or analyze a plurality of analytes. For example, a test platform 2 can house more than one test element, each specific for different analytes, such as two different test strips 3. The chemistry on the two different test strips can be different such that different reagents in the sample receiving chamber are desirable. In this way, using color coding alone, orientational coding or a combination thereof, the operator can engage the sample receiving 1 chamber with a test platform 2 such that sample dispensing at a defined or predetermined locus is accomplished. The outlet or outlets 72 for each key is illustrated.

As shown in FIG. 9B through FIG. 9F, a variety of keys 71 can be used to encode a sample collection and dispensing device of the present invention for use to engage an appropriate engaging structure 80. The reagent in a sample receiving chamber 1 can be tailored to the test being performed on the test element, which can be coded by the key 71 and the engaging structure 80.

FIG. 10A depicts a front view, FIG. 10B depicts a top view, and FIG. 10C depicts a bottom view of the male insert 102. A grooved ridge 105 encircles the opening or the proximal end 109. A stud 103 protrudes from the side wall of the cylinder shaft of the male insert 102. A male outlet port 106 is located at the distal end 110*a* of the male insert 102. One or more internal longitudinal ribs 107 are located inside the male insert 102. An internal incline 104 is located at the bottom of the male insert 102 to guide the flow of the content. An o-ring 108 is seated around the male outlet port 106 of the male insert 102 to prevent leakage.

FIG. 11A depicts a front view and FIG. 11B depicts a back view of the female receptor 111. The female receptor 111 has a base 112 with a notch 113 for proper attachment onto a test platform 120 on the present invention. An open groove guide 114 is situated along the side, which guides the stud 103 of the male insert 102. A female outlet port 115 is situated at the distal end 110*b* of the female receptor 111.

FIG. 12A depicts a top view and FIG. 12B depicts a side view on the bottom portion 121 of the test platform 120. One or more support structures 122 are located inside the bottom portion 121 for supporting the test device. One or more snap lock 123 mechanisms are situated around the inside of the bottom portion 121 to secure the top portion 131 to the bottom portion 121 of the test platform 120.

FIG. 13A depicts a top view and FIG. 13B depicts a side view of the top portion 131 of the test platform 120. The top portion 131 in this instant includes an engaging structure 132 with a stud 135 that can engage the notch 113 of the female receptor 111 of the sample receiving chamber of the present invention. The test result can be viewed through the test result window 133 and any trapped air from test reactions is vented out through the vent holes 134. The snap lock mechanisms 136 of the top portion 131 can engage the snap lock mechanism 123 of the bottom portion 121 to form the test platform 120.

SUMMARY

Figure 1:
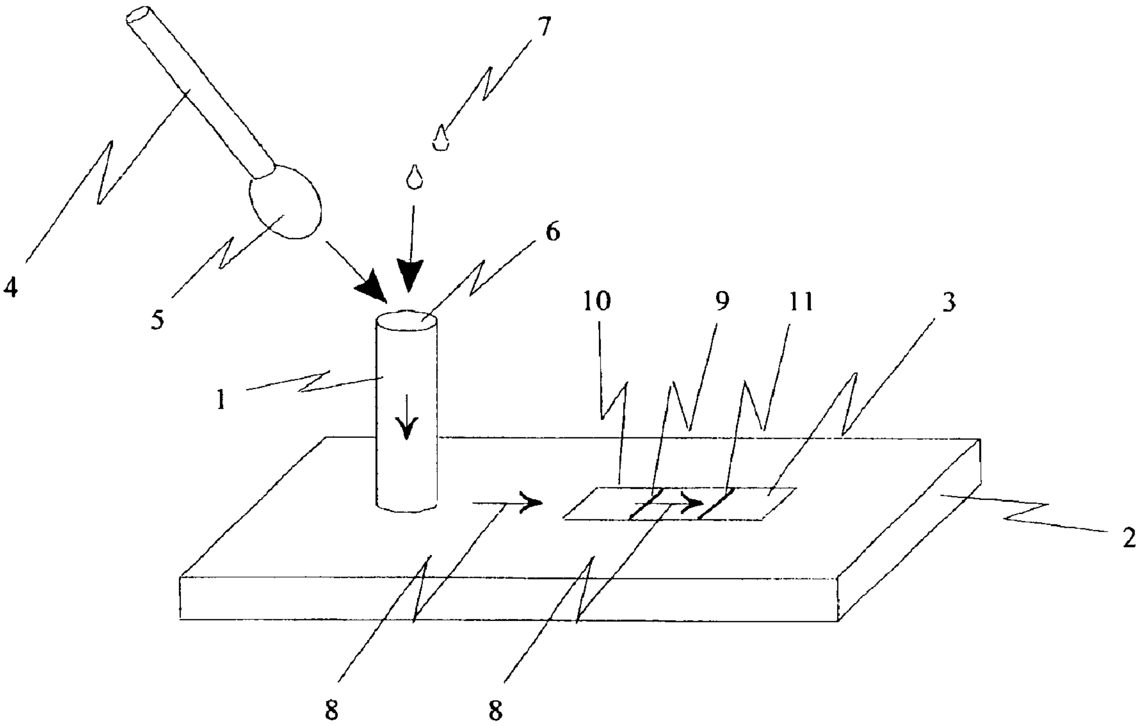
FIG. 1 depicts one aspect of a test device of the present invention in use. The sample receiving chamber 1 is engaged to the test platform 2 that houses a test element, in this case an immunochromatographic test strip 3. A swab 4, with the sample on the swab head 5, is inserted through an opening in the top or proximal end 6 the sample receiving chamber 1. A reagent 7 containing components for an appropriate test is deposited through the proximal opening 6 into the sample receiving chamber 1 where the sample is extracted into the reagent. The fluid mixture comes into fluid contact with a sample application area of the test strip 3 and wicked by capillary flow 8 along the test strip 3. The presence of a visible line at a detection zone 9 of the test strip 3, observed through an opening 10 of the test platform 2, indicates the presence of an analyte in the sample. The presence of a line at a control region 11 of the test strip 3 indicates a successful assay.

The present invention recognizes that it can be desirable to have a sample receiving chamber integral to, or engageable with, a test platform, such as a test platform that includes a test strip. The sample receiving chamber is preferably separate or separable from the test platform, but that need not be the case. Preferably, a fluid flow actuating or modulating device or structure, such as a valve separates the sample receiving chamber from the test platform. The present invention provides such a device and methods of use.

A first aspect of the present invention is a test device that includes a sample receiving chamber and a test platform that preferably includes a test element. The sample receiving chamber preferably engages the test platform and is optionally separable therefrom.

A second aspect of the present invention is a method of detecting an analyte in a sample, including: providing a sample, contacting the sample with a test device and detecting the analyte in the sample. The test device preferably includes a sample receiving chamber and a test platform that includes a test element. Preferably, the sample receiving chamber engages the test platform and optionally the sample receiving chamber is separable from the test platform.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Terms of orientation such as "up" and "down" or "upper" or "lower" and the like refer to orientation of the parts during use of the device. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings:

An element of the present invention is "integral to" another element of the present invention when the two elements are manufactured as a single piece.

An element of the present invention is "separate from" another element of the present invention when the two elements are manufactured as separate pieces.

"Proximal" refers to the upper end of a sample receiving chamber and provides an orifice for insertion of materials such as sample, sample collection device, and reagents into the sample receiving chamber.

"Distal" refers to the end of a sample receiving chamber that is opposite to and farthest from the proximal end of the sample receiving chamber and is that end that provides an outlet from the sample receiving chamber.

"Directly" means that one structure is in physical contact with another structure, or, when used in reference to a procedure, means that one process effects another process or structure without the involvement of an intermediate step or component.

"Indirectly" means that one structure is not in immediate physical contact with another structure, but rather contacts an intermediary structure that contacts the other structure. When used in reference to a procedure, "indirectly" means that one process effects another process or structure by means of an intermediate step or component.

A "reagent" can be any chemical, including organic compounds and inorganic compounds and combinations thereof. A reagent can be provided in gaseous, solid, or liquid form, or any combination thereof, and can be a component of a solution or a suspension. A reagent preferably includes fluids, such as buffers useful in methods of detecting analytes in a sample, such as anticoagulants, diluents, buffers, test reagents, specific binding members, detectable labels, enzymes and the like. A reagent can also include an extractant, such as a buffer or chemical, to extract an analyte from a sample or a sample collection device. For example, a buffer can be used to free biological components such as cells or etiological agents on or within a sample collection device, such as a swab. Alternatively, an extractant, such as an acid, can be use to extract analytes from the sample, such as LPS from bacteria.

A "barrier" is a thin piece of material that is not rigid. By "thin" it is meant that the thickness of the material is lesser that either its length or width. A "puncturable barrier" of the present invention can be punctured by a puncturing structure when brought into contact with a puncturable barrier with sufficient force. A puncturing structure can protrude through a puncturable barrier. Suitable materials for barriers include foils, plastics, and foil-plastic laminates.

A "key for engaging a test platform" or "key" of a sample receiving chamber of the present invention is a structure that can engage a second device, such as a test platform. A key can be integral to a sample receiving chamber of the present invention, or can be separate from a sample receiving chamber of the present invention and can engage a sample receiving chamber. Use of a key to engage a sample receiving chamber with a test platform can position a sample receiving chamber of the present invention such that sample can be dispensed into the appropriate area of a second device.

A "test element" is an element for analyzing a sample. A test element can be used to detect the presence and/or concentration of an analyte in a sample, or to determine the presence and/or numbers of one or more components of a sample, or to make a qualitative assessment of a sample. Test elements of the present invention include, but are not limited to, cuvettes, slides, lateral flow detection devices such as test strip devices, and columns.

A "lateral flow detection device" is a device that determines the presence and/or amount of an analyte in a liquid sample as the liquid sample moves through a matrix or material by lateral flow, such as an immunochromatographic device.

"Sample application aperture" refers to the portion of a test platform where an opening provides access to the portion of the test platform that receives the sample. For example, a sample application aperture can provide access to a sample application zone of a test strip, or a plurality of test strips, of a lateral flow detection device.

"Analyte" is the compound or composition to be measured that is capable of binding specifically to a ligand, receptor, or enzyme, usually an antibody or antigen such as a protein or drug, or a metabolite. The precise nature of antigenic and drug analytes together with numerous examples thereof are disclosed in U.S. Pat. No. 4,299,916 to Litman, et al., particularly columns 16 to 23, and in U.S. Pat. No. 4,275,149, columns 17 and 18, the disclosures of which are incorporated herein by reference. Analytes can include antibodies and receptors, including active fragments or fragments thereof. An analyte can include an analyte analogue, which is a derivative of an analyte, such as, for example, an analyte altered by chemical or biological methods, such as by the action of reactive chemicals, such as adulterants or enzymatic activity.

"Antibody" is an immunoglobulin, or derivative or fragment or active fragment thereof, having an area on the surface or in a cavity which specifically binds to and is thereby defined as complementary with a particular spatial and polar organization of another molecule. The antibody can be monoclonal or polyclonal and can be prepared by techniques that are well known in the art such as, for example, immunization of a host and collection of sera or hybrid cell line technology.

"Control analyte" is a compound present in the sample or reagent chamber that can be detected by an analysis device. Detection of the control analyte in the control zone indicates that fluid has moved throughout the analysis device.

"Sample" is any material to be tested for the presence and/or concentration of an analyte in a sample, or to determine the presence and/or numbers of one or more components of a sample, or to make a qualitative assessment of a sample. Examples of liquid samples that may be tested using a test device of the present invention include bodily fluids including blood, serum, plasma, saliva, urine, ocular fluid, semen, and spinal fluid; water samples, such as samples of water from oceans, seas, lakes, rivers, and the like, or samples from home, municipal, or industrial water sources, runoff water or sewage samples; and food samples, such as milk or wine. Viscous liquid, semi-solid, or solid specimens may be used to create liquid solutions, eluates, suspensions, or extracts that can be samples. For example, throat or genital swabs may be suspended in a liquid solution to make a sample. Samples can include a combination of liquids, solids, gasses, or any combination thereof, as, for example a suspension of cells in a buffer or solution. Samples can comprise biological materials, such as cells, microbes, organelles, and biochemical complexes. Liquid samples can be made from solid, semisolid or highly viscous materials, such as soils, fecal matter, tissues, organs, biological fluids or other samples that are not fluid in nature. For example, these solid or semi-solid samples can be mixed with an appropriate solution, such as a buffer, diluent, extraction buffer, or reagent. The sample can be macerated, frozen and thawed, or otherwise extracted to form a fluid sample. Residual particulates can be removed or reduced using conventional methods, such as filtration or centrifugation.

Other technical terms used herein have their ordinary meaning in the art that they are used, as exemplified by a variety of technical dictionaries.

Introduction

The present invention recognizes that it can be desirable to have a sample receiving chamber integral to or engageable with a test platform, such as a test platform that includes a test strip. The sample receiving chamber is preferably separate or separable from the test platform, but that need not be the case. Preferably, a fluid flow actuating or modulating device or structure such as a valve separates the sample receiving chamber from the test platform. More preferable, the valve structure can be positioned on the test platform or at the distal or outlet end of the sample receiving chamber whereupon when engaged, the valve structure can actuate or modulate flow from the sample receiving chamber into the test platform. The present invention provides such a device and methods of use.

As a non-limiting introduction to the breath of the present invention, the present invention includes several general and useful aspects, including:

1. a test device that includes a sample receiving chamber and a test platform that includes a test element, where the sample chamber preferably engages the test platform and optionally is separable therefrom; and
2. a method of detecting an analyte in a sample, including providing a sample, contacting the sample with a test device of the present invention and detecting the analyte in the sample, if present.

These aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention.

I Test Device

Figure 2:
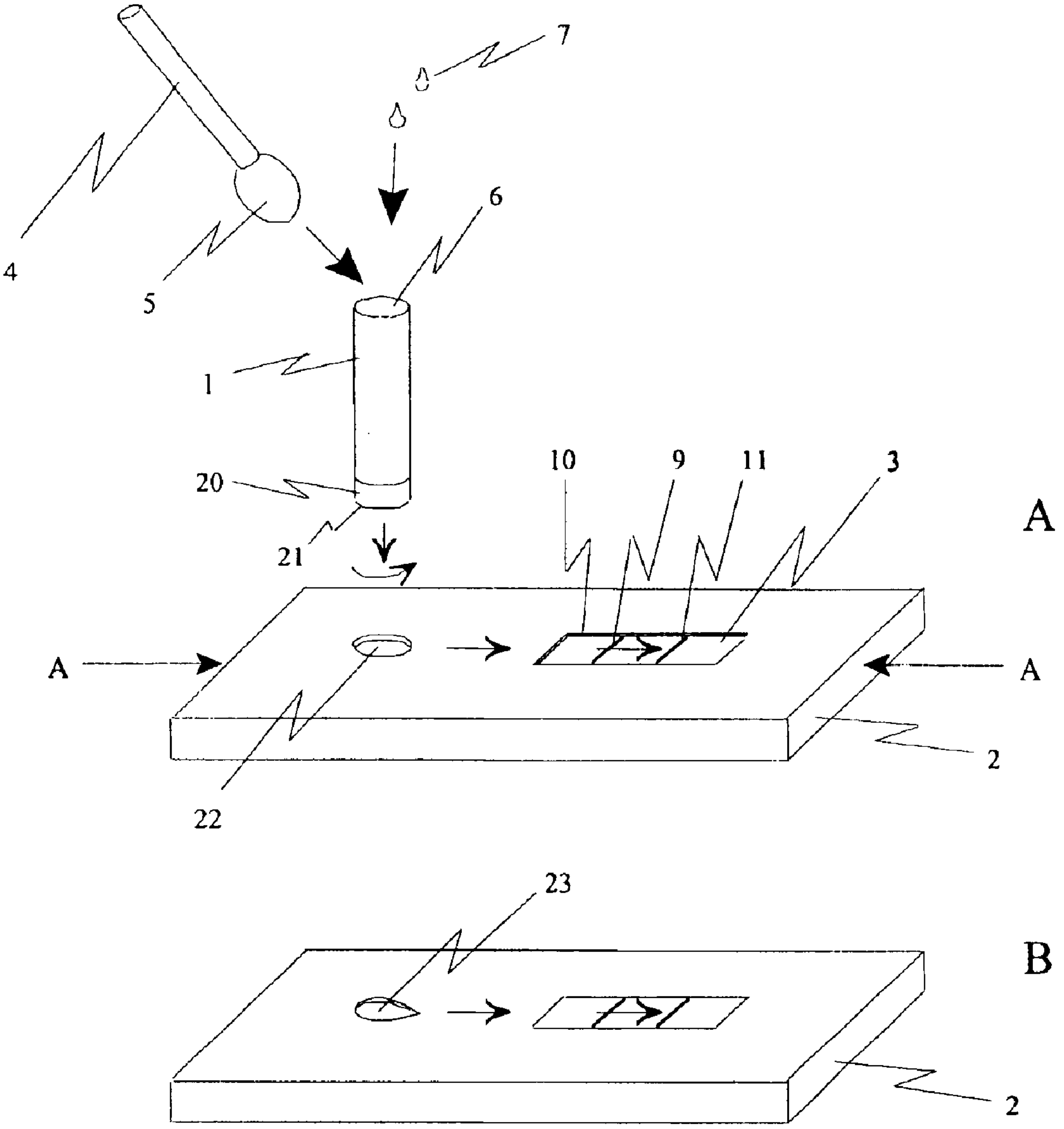
FIG. 2A depicts one aspect of a test device of the present invention, wherein the sample receiving chamber 1 is separate from the test platform 2 housing an immunochromatographic test strip 3. A valve structure 20 is located at the distal end of the disengaged sample receiving chamber 1 such that when in the closed position no fluid can flow out of the bottom or distal end 21 of the sample receiving chamber 1. A reagent 7 containing components for an appropriate test is deposited via the proximal opening 6 into the sample receiving chamber 1 and a swab 4, with the sample on the swab head 5, is inserted through the opening at the top or proximal end 6 the sample receiving chamber 1. The distal end 21 of the sample receiving chamber 1 engages the test platform 2 at the aperture 22 such that it is substantially perpendicular to the test platform 2. After incubation of the sample in reagent the valve 20 is rotated such that the valve is opened and the fluid contents are released at a controlled flow onto a sample application area of the test strip 3. The fluid is wicked by capillary flow 8 along the test strip 3 and the presence of a visible line at a detection zone 9 of the test strip 3, observed through an opening 10 of the test platform 2, indicates the presence of a specific analyte in the sample. The presence of a line at a control region 11 of the test strip 3 indicates a successful assay.
FIG. 2B depicts a test platform 2 with an aperture 23 the shape of which, in this instance, is partially circular on one side with a triangular edge on the other side of the aperture such that the aperture 23 can only accept and support a sample receiving chamber with a specific key structure at its distal end.

The present invention includes a test device that includes a sample receiving chamber 1 and a test platform 2 that preferably includes a test element. The sample receiving chamber 1 preferably engages the test platform 2 and is optionally separable therefrom as depicted in FIG. 1 and FIG. 2. When engaged the sample collection chamber 1 and test platform 2 are preferably substantially perpendicular. The sample receiving chamber 1 can accept a sample directly or by way of a sample collection device such as, but not limited to, a rod, spoon, spatula, knife, brush, or fabric, but is preferably a swab 4. Optionally the sample receiving chamber 1 can contain one or more reagents prior to transfer of the sample. In another aspect of the present invention one or more reagents 7 can be added to the sample receiving chamber before transfer, during transfer or post transfer, of the sample into the sample receiving chamber 1. The sample can incubate with the reagent or reagents 7 for an approximate or specific period of time prior to transfer into the sample receiving chamber 1 or can incubate within the sample receiving chamber 1. The contents of the sample receiving chamber 1, when engaged with the test platform 2, can be released into the test platform 2 by way of structures such as, but not limited to, the opening of a valve or penetration of a rupturable barrier of the sample receiving chamber 1. Upon release from the sample receiving chamber 1 the sample, with or without one or more reagents, can come into fluid contact with the test platform 2 and thereby a test element associated with the test platform such as, but not limited to, an immunchromatographic test strip 3.

Sample Receiving Chamber

The sample receiving chamber 1 includes a proximal end 6 and a distal end 21, wherein the proximal end 6 can receive a sample and the distal end 21 can directly or indirectly engage a test platform 2 of the present invention. In one aspect the contents of a sample receiving chamber 1 can be released through the distal end of the sample receiving chamber 1, preferably into a test platform 2 as depicted in FIG. 1. The sample receiving chamber 1 can be of any geometric shape or dimension such as, but not limited to, triangular, spherical, oval, square, rectangular, pentagonal, hexagonal, heptagonal, octagonal, or any polygon, or non-geometric shape such as kidney or bean shaped, but is preferably substantially cylindrical. The size of the sample receiving chamber 1, encompassing such dimensions as the width, height and diameter of the sample receiving chamber 1 can be such that an indiscriminate or predetermined volume of a sample can be efficiently transferred to the sample receiving chamber 1, or can readily accept insertion of a sample and sample collection device 5 and if desirable, one or more reagents 7. The proximal or receiving end 6 of the sample receiving chamber 1 can be flared, funnel shaped or otherwise molded such that a sample can readily and accurately be transferred into the sample receiving chamber 1, but this need not be the case. Alternatively a funnel shaped adaptor can be separable and directly or indirectly engage the proximal end 6 of the sample receiving chamber 1.

The sample receiving chamber 1 can be made of suitable material such as, but not limited to, glass, ceramics, metals, plastics, polymers, or copolymers, or any combination thereof but preferably comprises a plastic, polymer or copolymer such as those that are resistant to breakage, such as polypropylene, polyallomer, polycarbonate or cycloolefins or cycloolefin copolymers. A sample receiving chamber 1 can be made by appropriate manufacturing methods, such as, but not limited to, injection molding, blow molding, machining or press molding.

A sample can be fluid, solid or gaseous, or any combination thereof. In one aspect of the present invention a sample can be transferred to, and flow through or be retained in, and can subsequently be released from, the sample receiving chamber 1. Transfer of a sample into the sample receiving chamber 1 can be by various techniques such as, but not limited to pipetting, pouring, decanting, dropping or streaming. Optionally, a sample can be mixed with one or more reagents. Mixture can occur prior to transfer into the sample receiving chamber, but preferably the sample and one or more reagents 7 can be mixed in the sample receiving chamber 1. Reagents can include one or more salts, chelators, anticoagulants, detergents, stabilizers, diluents, buffering agents, enzymes, cofactors, specific binding members, labels, and the like. The one or more reagents can be compounds that facilitate analysis of a sample, but this is not a requirement of the present invention.

In another aspect of the present invention a sample can be transferred to the sample receiving chamber 1 by way of a sample collection device such as, but not limited to, a rod, spoon, spatula, knife, brush, or fabric, but is preferably a swab 4. In one embodiment of the present invention a sample can be collected onto the sample collection device, for example by dipping, submerging, soaking, dabbing, scraping, swiping or wiping. The sample collection device with sample can then be transferred or otherwise placed or inserted into the sample receiving chamber 1, optionally with one or more reagents in the sample receiving chamber 1 or subsequently added to the sample receiving chamber 1.

Figure 5:
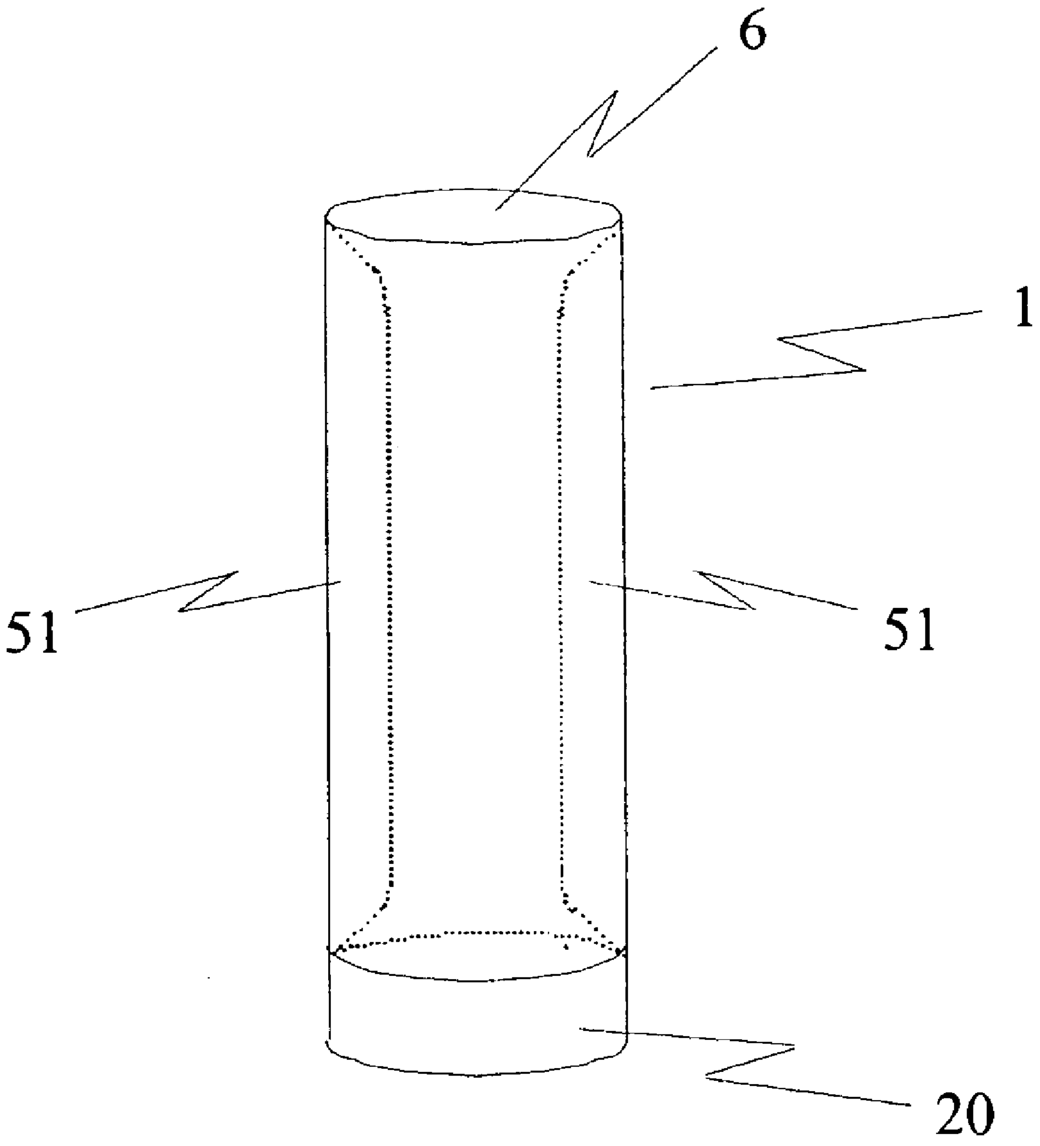
FIG. 5 depicts a sample receiving chamber 1 of the present invention showing internal longitudinal ribs 51 that alternately constrict the interior of the chamber.

In one preferred aspect of the present invention one or more concentric or longitudinal ribs, ridges or edges 51 can be arranged along the interior of the sample receiving chamber 1 as depicted in FIG. 5. The one or more structures 51 can facilitate extraction of a sample from the sample receiving chamber 1 to mix with one or more reagents in the sample receiving chamber 1. For example, when a swab 4 is used to collect a sample, such as by dipping the swab head 5 into a blood sample, the swab 4 can be inserted into the sample receiving chamber 1 with one or more longitudinal ridges 51 aligned along the inside wall. By rotating the swab 4 different portions of the swab head 5 can be alternately compressed and decompressed by the one or more longitudinal ridges 51 to facilitate release of the blood into the sample receiving chamber 1.

In another embodiment one or more filters can be positioned within the sample receiving chamber 1, preferably at or near the distal end 21 of the sample receiving chamber 1. When a sample or sample and reagent flow through, or are released from, the sample receiving chamber 1, aggregates or particulate matter can be trapped by the one or more filters and prevented from exiting the sample receiving chamber 1. For example, blood cells can be trapped from a whole blood sample by the one or more filters. Filters can be composed of various materials such as, but not limited to, paper, cellulose and cellulose derivatives, nitrocellulose, polymers, charcoal, glass fibers, organic fibers, cotton, hair, wool, fur, or lint, or in any combination thereof.

In one aspect of the test device of the present invention the sample receiving chamber 1 can be separate from the test platform 2. The distal end 21 of the sample receiving chamber 1 can engage a test platform 2, preferably at an opening or aperture 22 of the test platform 2, such that they are substantially perpendicular to each other (See for example FIG. 2). The sample receiving chamber 1 can be inserted into an aperture 22 of the test platform 2 in order to engage the test platform 2. Insertion can be by various structures such as, but not limited to, slide, push, snap, twist, bayonet fit, or screw the distal end 21 of the sample receiving chamber 1 into an aperture 22 of the test platform 2. For example, the aperture 22 can have a spiral path along the inner wall and threads can be formed along the external distal region of the sample receiving chamber 1 such that they can be attached by a twisting or screwing motion. In the case of a snap insertion a groove can be formed along the inside wall of the aperture 22 and a raised ridge can encircle the outside distal region of the sample receiving chamber 1 such that the sample receiving chamber 1 can be slid into the aperture 22 and the ridge snaps or locks into the groove of the aperture 22. Alternatively, the aperture 22 can be encircled by a raised edge, with or without grooves or threads, over which the sample receiving chamber 1 can be slid, snapped or screwed to engage the test platform 2. Grooves or threads can be machined into the appropriate component during manufacture using techniques commonly used in the art. A snap or snug fit can confer a reassuring sound or feel so that the operator is confident that the sample receiving chamber 1 and the test platform 2 have engaged properly. Optionally, one or more structures such as one or more gaskets or one or more O-rings 65, or any combination of such structures, can be positioned at the intersection of the sample receiving chamber 1 and the test platform 2 to reduce or prevent any leakage.

In a preferred aspect of the test device of the present invention one or more valve structures 20 can be positioned such that the one or more valve structures can actuate flow from the sample receiving chamber 1 into the test platform 2 of the test device. One embodiment can have a valve structure 20 that can be separate and function as an intermediary or adaptor structure between the sample receiving chamber 1 and the test platform 2. For example the lower side or end of a valve structure, separate from either a sample receiving chamber 1 and a test platform 2, can be positioned and engaged onto a test platform 2, at an aperture 22, and the distal or outlet end of a sample receiving chamber 1 can be inserted and secured into the upper portion of the valve structure. Alternatively, the valve structure can be directly engaged to the aperture 22 of the test platform 2. Alternatively, the valve structure 20 can be directly engaged to the distal or outlet end of the sample receiving chamber 1, or the sample receiving chamber 1 can itself be comprised of a valve structure, whereupon when engaged to the test platform 2, the valve structure can actuate flow from the sample receiving chamber 1 into the test platform 2.

Figure 4:
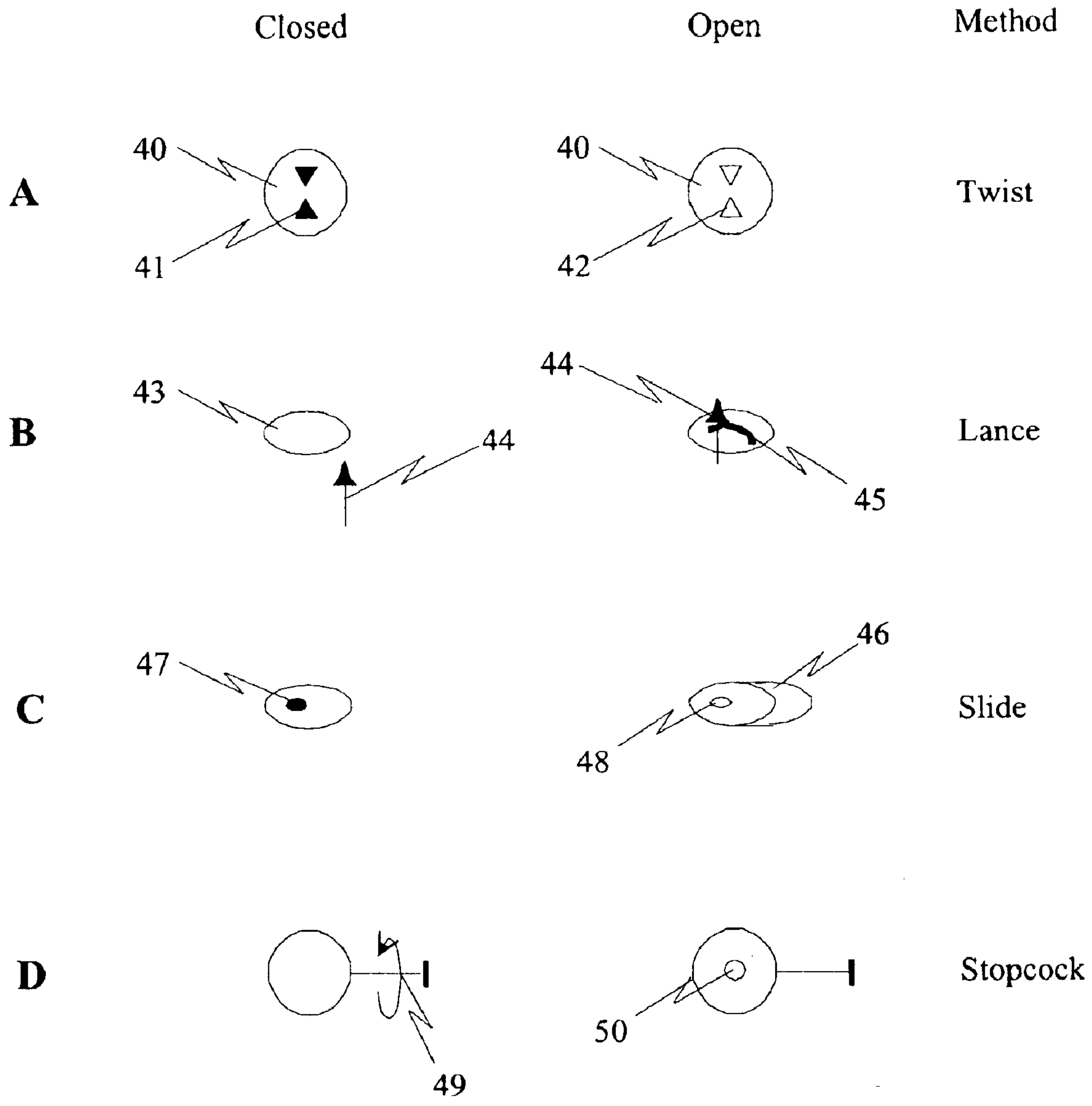
FIG. 4 depicts several mechanical structures that can be located, as viewed, at or near the distal end of a sample receiving chamber. In the closed position the contents are retained in a sample receiving chamber. In the opened or partially opened position the contents are released in a regulated flow of a sample, or a sample and reagent, from a sample receiving chamber of the present invention. For example.

The valve can be of any type as recognized in the art such as, but not limited to, a rotary, stopcock, gate, ball, needle, butterfly, pinch, bellows, piston, slide, plug, diverter, or actuator valve. When the valve is in the closed position, as depicted for several examples in FIG. 4, and the sample receiving chamber 1 sufficiently vertical, a sample or sample and reagent can be retained in the sample receiving chamber 1. When the valve is in the open position the contents of the sample receiving chamber 1 can be released, for example by gravity flow. In a preferred embodiment of the present invention the valve structure 20 can be opened to release the contents from the distal or outlet end 21 of the sample receiving chamber 1 such that the flow can be actuated, regulated or modulated. In another aspect of the present invention the valve mechanism 20 can be closed such that the sample or sample and one or more reagents can be retained in the sample receiving chamber 1 for any length of time. The valve structure 20 can then be mechanically, fully or partially, opened to release the contents through the distal or outlet end 21 of the of the sample receiving chamber 1 into the test platform 2 of the test device, optionally at a regulated or modulated rate. In a preferred embodiment the sample receiving chamber 1 can be engaged to a second device, for example the test platform 2 of the present invention, such that opening of the valve structure 20 can release the contents into the second device. The valve structure 20 at the distal end of the sample receiving chamber 1 can be opened to release the contents by various means such as, but not limited to, opening a stopcock or by turning, rotating, twisting or sliding the valve structure such that the valve can be opened to allow fluid communication into the test platform 2 (see of example FIG. 4).

Figure 6:
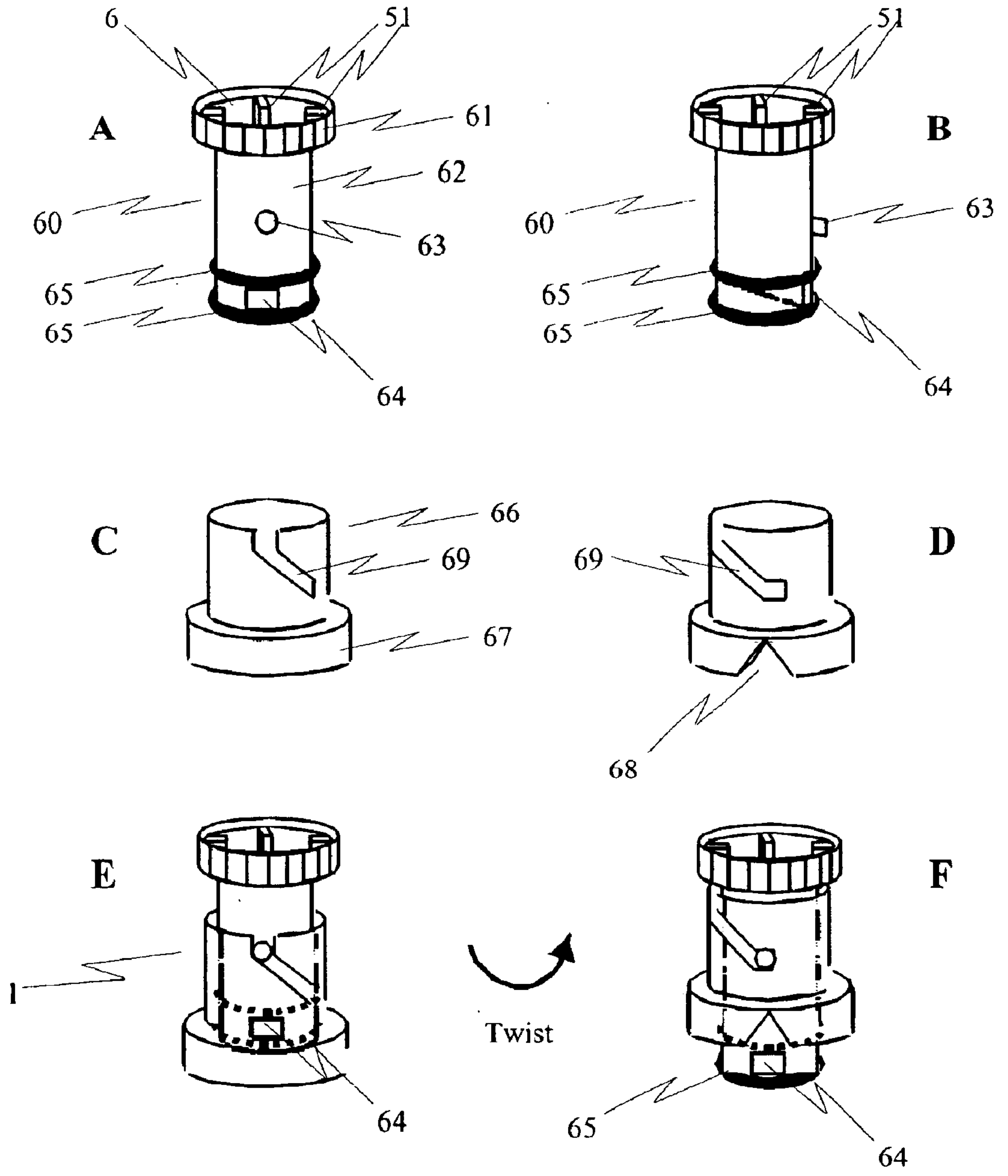
FIG. 6 depicts one aspect of a sample receiving chamber 1 of the present invention.

An example of a sample receiving chamber 1 comprising a valve is depicted in FIG. 6. In this embodiment the sample receiving chamber 1 is comprised of a male insert 60 and female receptor 66. The female receptor 66 is a tube-like structure with a base 67 that can be engaged to an aperture 22 of a test device. The male insert 60 is cylindrical with the bottom or distal end stopped or closed off, for example during manufacture, and having an outlet port 64 situated along the side wall 62 at the distal or lower region of the male insert 60. The male insert 60 can be introduced into the female receptor 66 such a stud 63 protruding from the side of the male insert 60 fits into a groove guide 69 of the female receptor 66. When in the closed position the stud 63 of the male insert 60 sits at the top of the upper region of the female receptor groove guide 69. In this position the outlet port 64, flanked by one or more O-rings 65 to reduce or prevent leakage, faces the inner wall of the female receptor 66 such that fluid is retained in the sample receiving chamber 1. To open the sample receiving chamber 1 valve structure an operator can rotate the upper region of the male insert 60 whereby the groove guide 69 slides the stud 63, and therefore the male insert 60, in a downward direction such that the outlet port 64 protrudes below the female receptor 66 releasing the contents of the sample receiving chamber 1 into the test platform 2, preferably onto a sample application zone 30 of a test element, preferably a test strip 3.

Figure 10:
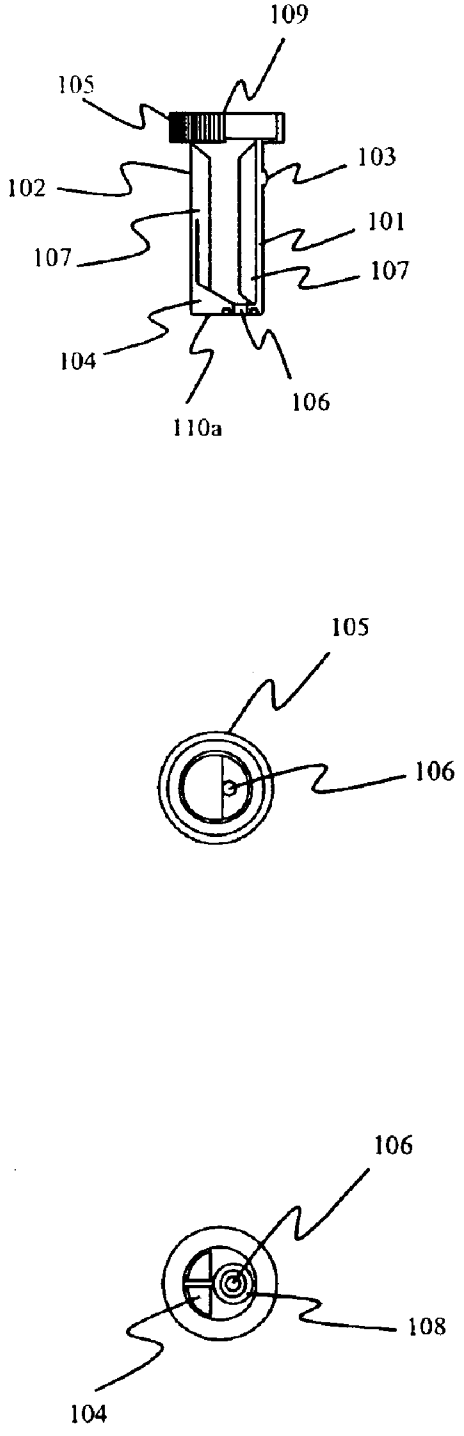
FIG. 10 depicts one aspect of the male insert 102 of an alternative sample receiving chamber 101 configuration of the present invention.
Figure 11:
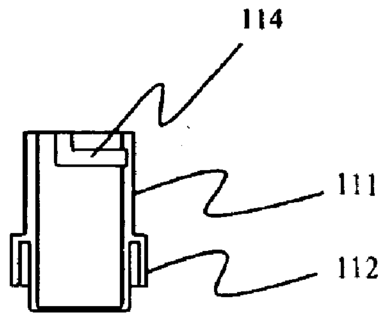
FIG. 11 depicts one aspect of a female receptor 111 of a sample receiving chamber 101 of the present invention.
Figure 11:
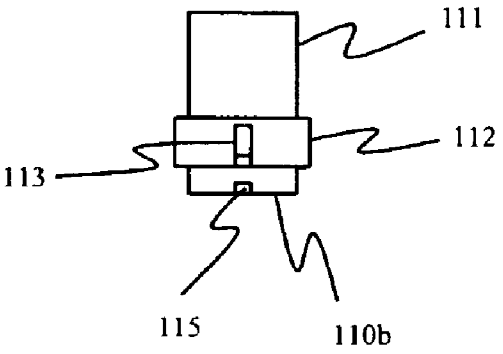
Figure 12:
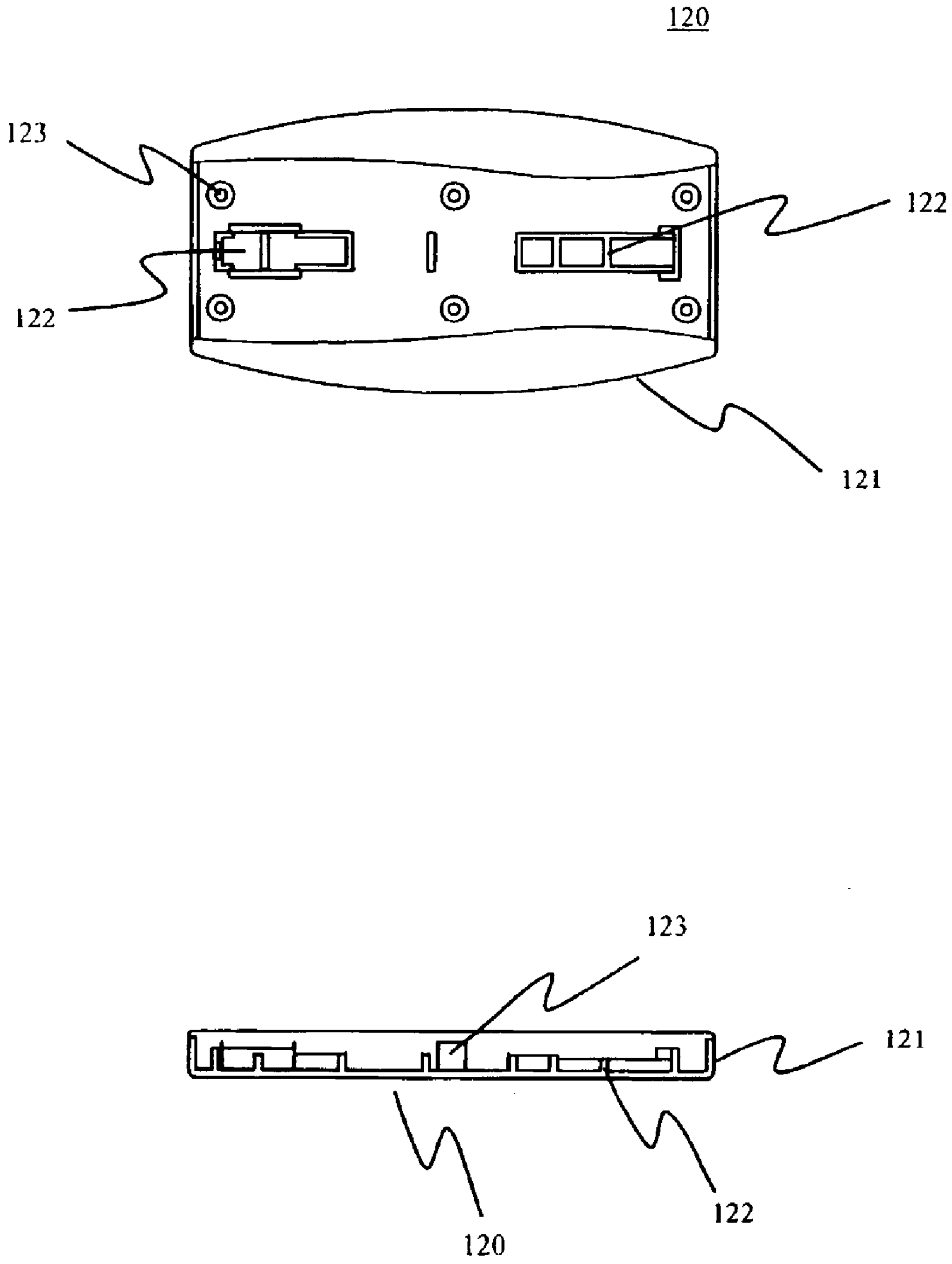
FIG. 12 depicts one aspect of the bottom portion of a test platform 120 of the present invention.
Figure 13:
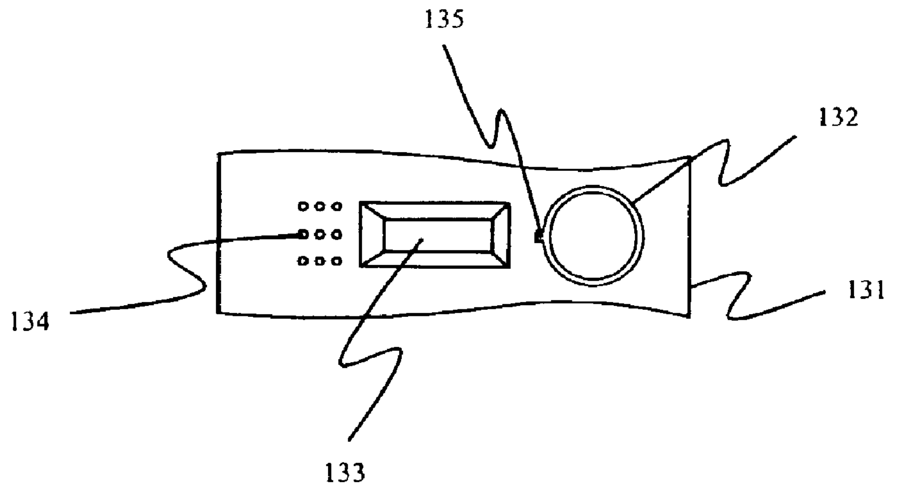
FIG. 13 depicts one aspect of the top portion of a test platform 120.
Figure 13:
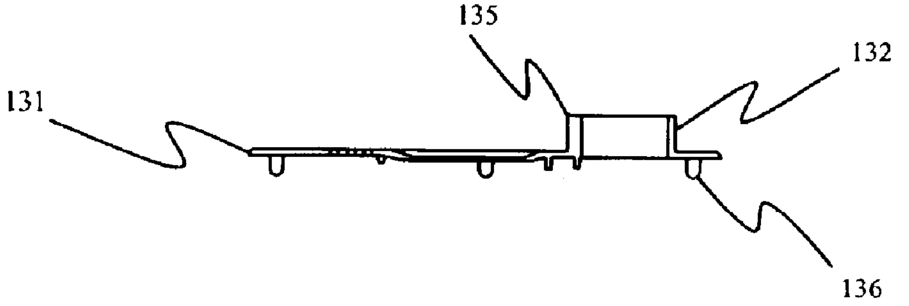

Another example of a sample receiving chamber 101 comprising a valve structure is depicted in FIG. 10 and FIG. 11. The male insert 102 having a male outlet port 106 is positioned within a female receptor 111 having a female outlet port 115. In the open position the male outlet port 106 is substantially or approximately aligned with the female outlet port 115 such that the sample or a portion of the sample may exit the sample receiving chamber 101 though the male outlet port 106 then proceed through the female outlet port 111 and enter the test platform 120. Sample flow may be prevented or stopped by placing the sample receiving chamber 101 in the closed position which may include discontinuing the alignment between the male outlet port 106 and the female outlet port 115. The test device may be returned to the open position by again approximately or substantially aligning the male outlet port 106 with the female outlet port 115 such that the male outlet port 106 and female outlet port 115 are in fluid communication.

A sealing structure such as an O-ring 108 may be positioned between the outer surface of the male insert 102 and the inner surface of the female receptor 111. The sealing structure obstructs fluid communication between the male outlet port 106 and female outlet port 115 when the test device is placed in the closed position by compressive forces applied against the sealing structure by the male insert 106 and female receptor 115. The O-ring 108 may be seated around the male outlet port 106 thereby moving in concert with the male outlet port 106 and sealing the male outlet port 106 when not in substantial alignment with the female outlet port 115. The present invention also envisions sealing structure alternatives such as but not limited to a disc-like structure affixed to the female receptor 111 and having an aperture in alignment with the female outlet port 115 such that the male outlet port 106 is sealed against the disc-like structure unless in substantial alignment with the female outlet port 115 and therefore the aperture of the sealing structure.

The present invention envisions the male outlet port 106 and female outlet port 115 may have a wide variety of sizes and shapes. The size and shape of the male outlet port 106 and female outlet port 115 may be complimentary to one another however this is not required. Moreover the size and shape desired may depend on multiple factors such as but not limited to physical characteristics of the sample and the flow rate desired from the sample receiving chamber 101.

For example varying the size of the male outlet port 106 and female outlet port 115 may be desirable when the sample comprises a mixture of compounds having different sizes. The size of male outlet port 106 or female outlet port 115 may be altered to take advantage of size exclusion technologies. For example, a sample comprising a mixture of compounds having different sizes may be preferentially separated by modification of the size of the male outlet port 106 or female outlet port 115. Alternatively when the sample comprises a compound in its solid and liquid states, the liquid state may be preferentially selected for by choosing a male outlet port 106 or female outlet port 115 that excludes the solid state and allows passage of the liquid state. However, when a sealing structure such as an O-ring 108 is seated around the male outlet port 105, the male outlet port 106 is generally smaller in size than the O-ring 108.

The size of the male outlet port 106 and the female outlet port 115 may also be chosen at least in part by the flow rate desired from the sample receiving chamber 101. Generally, smaller apertures have a slower flow rate than larger apertures. A slower flow rate may therefore be preferred when aliquoting a single sample into multiple test strips 3 such as but not limited to a configuration having a single male outlet port 106 and multiple female outlet ports 115 such that each female outlet port 115 transfers a portion of the sample to an independent test strip 3. Slower flow rates may also be desired when the volume of the sample receiving chamber 101 is greater than the loadable volume of the particular test strip 3 chosen. In this instance the slower flow rate allows the user time to interrupt or halt the flow of sample from the sample receiving chamber 101 prior to overloading the particular test strip 3. To further assist the user indicia such as volume markers may be placed within the sample receiving chamber 101 to represent the volume remaining or volume released from the sample receiving chamber 101.

The shape of a male outlet port 106 and female outlet port 115 may be a symmetric shape such as but not limited to elliptical or rectangular or may be an asymmetric shape. Factors that determine the desired shape of the male outlet port 106 and female outlet port 115 may include but are not limited to the manufacturing capabilities and preferences of the producer. For example, generally circular shapes are commonly used in the manufacturing industry in the placement of an aperture because of the prevalence of appropriate tools such as but not limited to drill bits and insertion rods. In addition O-rings 108 are often provided in a circular shape which may lead a manufacturer to prefer the use of a similarly shaped male outlet port 106 or female outlet port 115 however this is not required.

The present invention envisions a variety of configurations for the male outlet port 106 and female outlet port 115. These configurations include but are not limited to the male outlet port 106 positioned along the distal end 110*a* of the male insert 102 and the female outlet port 115 positioned along the distal end 110*b* of the female receptor 111; the male outlet port 106 positioned along the sidewall generally located at the distal end 110*a* of the male insert 102 and the female outlet port 115 positioned along the sidewall generally located at the distal end 110*b* of the female receptor 111; and the male outlet port 106 positioned along the sidewall generally located at the distal end 110*a* of the male insert 102 and the female outlet port 115 positioned along the distal end 110*b* of the female receptor 111. A stud 103 positioned on the outer sidewall of the male insert 102 and generally complimentary to an open groove guide 114 along the female receptor 111 may provide the user guidance in correctly opening, closing and/or locking the device in a desired position.

In one configuration the male outlet port 106 is positioned along the distal end 110*a* of the male insert 102 such as at the base of the internal incline 104 and the female outlet port 115 is positioned along the distal end 110*b* of the female receptor 111 as depicted in FIG. 10 and FIG. 11. In this configuration the test device is in the open position when the male outlet port 106 is in substantial or approximate vertical alignment with the female outlet port 115. The test device is in the closed position when the male outlet port 106 is removed from approximate or substantial vertical alignment with the female outlet port 115. Reducing and stopping the flow of sample may be performed by a variety of techniques such as but not limited to twisting the grooved ridge 105 such that the O-ring 108 compresses and slides along the distal end 110*b* of the female receptor 111. The present invention envisions alternative methods to compress and position the O-ring 108 against the distal end 110*b* of the female receptor 111 such as pushing or pulling either the male insert 102 or the female receptor 111 generally horizontally or vertically against one another thereby sealing the male outlet port 106.

In another configuration the male outlet port 105 is positioned along the sidewall generally located at the distal end 110*a* of the male insert 102 and the female outlet port 115 is positioned along the sidewall generally located at the distal end 110*b* of the female receptor 111. The user may prefer the male outlet port 105 to be positioned along the sidewall when the sample includes debris or particulates that may tend to settle on the bottom of the sample receiving chamber 101 and are not to be transferred to the test platform 120. In this configuration the device is placed in the open position by horizontally aligning the male outlet port 106 and the female outlet port 115. The closed position may be accomplished using techniques such as altering the vertical placement of the male insert 102 or the female receptor 111 such as by lifting generally upward, pushing generally downward or a twisting motion along an inclined thread. The present invention also encompasses placing the device in the closed position by altering the perimeter positioning of the male outlet port 106 or female outlet port 115 such as by twisting the male insert 102 or female receptor 111 along the same horizontal plane.

In another configuration the male outlet port 106 is positioned along the sidewall generally located at the distal end 110*a* of the male insert 102 and the female outlet port 115 is positioned along the distal end 110*b* of the female receptor 111 such that when the test device is in the open position a sample may exit the male outlet port 106 generally horizontally then migrate generally downward between the male insert 102 and female receptor 111 and generally downward through the female outlet port 115. In this configuration a structure such as a groove along the inner sidewall of the female receptor 111 may provide guidance to the female outlet port 115. In the closed position the male outlet port 106 may be blocked from fluid communication with the female outlet port 115 using a variety of techniques such as twisting the male insert 102 and therefore rotating the male outlet port 106 and O-ring 108 along the sidewall of the female receptor 111 until the male outlet port 106 and female outlet port 115 are not in direct or indirect communication and the O-ring 108 is compressed against the inner side wall of the female receptor 111.

In another aspect of the test device of the present invention the distal end 21 of the sample receiving chamber 1 can include a barrier to contain contents within the sample receiving chamber 1 when in vertical position. The barrier can be flush with, or recessed within, the distal portion 21 of the sample receiving chamber 1. In a preferred embodiment the barrier is puncturable by a barrier puncturing device. A puncturable barrier can include any material that can be punctured by a puncturing or barrier rupturing device of the present invention, that is not substantially water permeable, water permeable, substantially air permeable or air permeable. Suitable materials include polymers or copolymers, such as for example polypropylene, polycarbonate, cycloolifins, cycloolifin copolymers, foils, and plastic/foil laminates. In a more preferred embodiment the one or more barrier puncturing devices can be associated with a test platform 2 of the present invention such that when the distal or outlet end 21 of the sample receiving chamber 1 engages the test platform 2 the barrier is ruptured or punctured such that the contents of the sample receiving chamber 1 are released into the test platform 2. For example see FIG. 4.

In another embodiment a membrane at or near the distal end 21 of the sample receiving chamber 1 can be dissolved over time after coming into fluid contact with a sample or sample and reagent. Such a membrane can be formed of a material such as, but not limited to, polysaccharides, starches, gelatins, plastics, or the like, or any combination thereof. The thickness of the membrane can affect the rate at which the membrane can be dissolved thereby allowing for an incubation period prior to release of sample or sample and one or more reagents from the sample receiving chamber 1.

In another aspect of the present invention a predetermined amount of one or more reagents can be prepackaged in the sample receiving chamber 1. In one aspect, a valve structure 20 at the distal end of the sample receiving chamber 1 can be closed and the proximal, or insertion, end 6 can be sealed by a removable or puncturable barrier, cover, or seal. In another embodiment one or more puncturable barriers situated within the sample receiving chamber 1 can separate or sequester a predetermined volume or volumes of one or more reagents. A removable cover can be for example a cap or screw-top. The cap or screw-top can be made of any appropriate material such as, but not limited to, metal or plastic, or any combination thereof. A puncturable barrier, cover or seal can be made of materials such as, but is not limited to, plastic, foil, membrane or cellophane, or any combination thereof. In one aspect, a puncturable seal can be at or near the proximal end of the sample receiving chamber 1, for example recessed within the sample receiving chamber 1. A puncturable barrier, cover or seal is substantially water soluble, water permeable, substantially air permeable or air permeable. Suitable materials for a puncturable barrier or membrane include polymers or copolymers, such as for example polypropylene, polycarbonate, cycloolifins, cycloolifin copolymers, foils, and plastic/foil laminates. Alternatively the one or more reagents can be separably packaged in a breakable or rupturable material, for example capsules, pouches, or balloons such that one or more reagent containing packages can be added to the sample receiving chamber 1 and punctured or ruptured by a barrier rupturing device or sample collection device.

In one aspect of the present invention a puncturing device such as, but not limited to a rod, needle, spear or spear-like structure can be inserted and withdrawn, one or more times, at the proximal, or insertional, end 6 of the sample receiving chamber 1 such that a seal or puncturable barrier is punctured, torn, ripped or removed to allow insertion of the sample. In another embodiment the puncturing device can be used to rupture the one or more puncturable barriers within the sample receiving chamber 1 and a sample or sample and one or more additional reagents are inserted into the sample receiving chamber 1. In a preferred embodiment a sample collection device can be used as the puncturing device. In a more preferred embodiment the sample collection device with sample can be used as the puncturing device whereby the sample and sample collection device are inserted into the sample receiving chamber 1 and the sample can mix with one or more reagents. In another embodiment one or more reagent containing packages, such as a capsule, pouch or balloon, that can be broken, ruptured or torn to release the contents of the respective packages can be compromised prior to insertion of the contents into the sample receiving chamber 1. For example a pouch can be torn and from which a reagent 7 can be transferred into the sample receiving chamber 1. Transfer can be by various techniques such as, but not limited to pipetting, poring or dropping the one or more reagents into the proximal, or insertional, end 6 of the sample receiving chamber 1. In another example a capsule containing reagent can be positioned over the proximal end of a sample receiving chamber 1 and crushed, such as between finger and thumb of an operator, and thereby infuse the sample receiving chamber 1 with the reagent.

A sample receiving chamber 1 of the present invention can optionally include a key for engaging a second device, preferably a test platform 2 of the present invention. Use of a key to engage a sample receiving chamber 1 with a test platform 2 can position a sample receiving chamber 1 and test platform 2 of the present invention such that sample, optionally mixed with one or more reagents, can be dispensed into the appropriate area of a second device, preferably a test platform 2.

Figure 7:
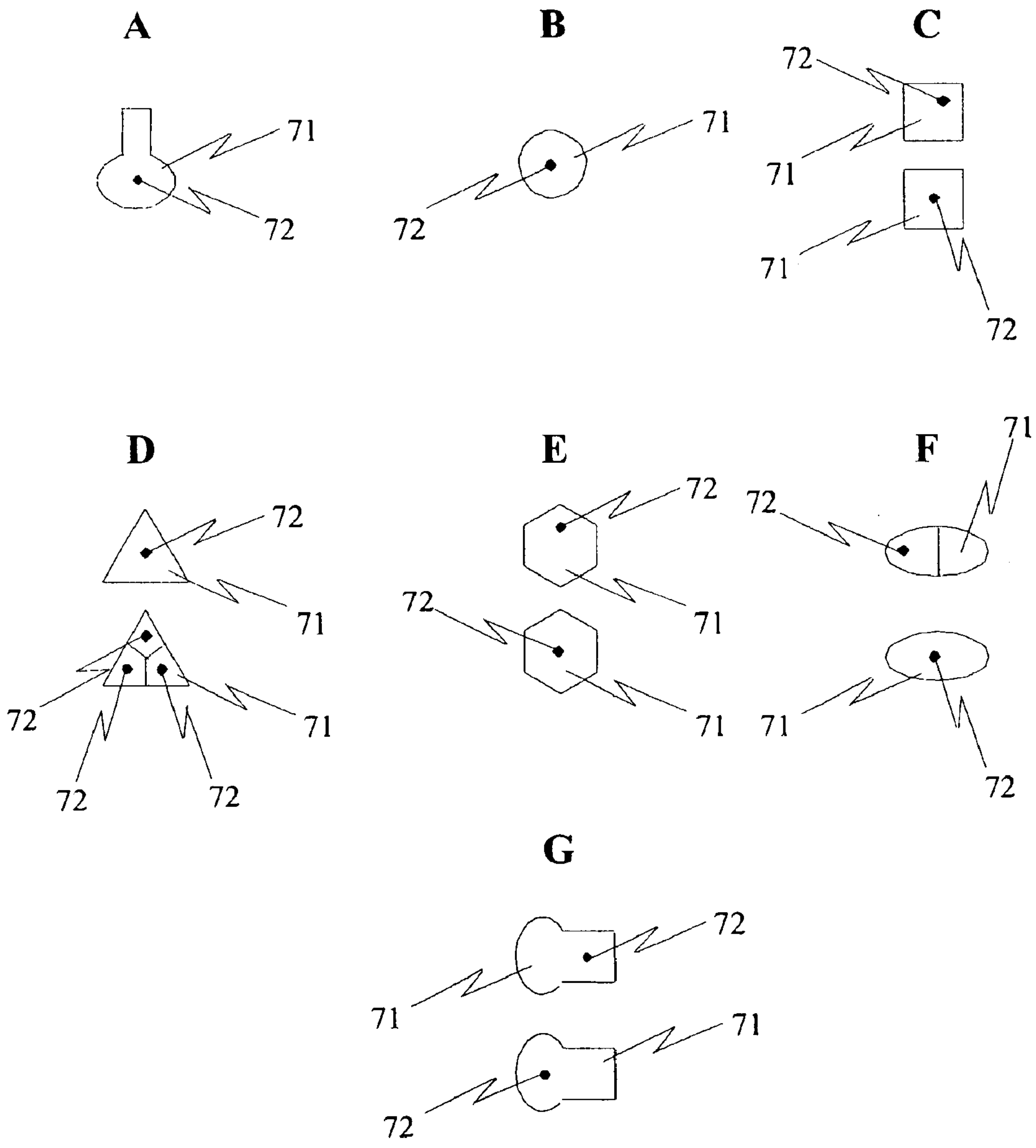
FIG. 7 depicts several designs for keys that can be used in the present invention, preferably for engaging or orienting the sample receiving chamber 1 with a test platform 2. For example.

A key can be integral to a sample receiving chamber 1 of the present invention, or can be separate and can engage a sample receiving chamber 1. Preferably, a key is positioned at or near the distal end 21 of the sample receiving chamber 1. Preferably, a key can be inserted into an aperture 23 of a test platform 2 of the present invention and turned or pushed into a position that locks or fixes the sample receiving chamber 1 and test platform 2 in position to dispense contents of the sample receiving chamber 1 into the test platform 2 and thereby onto a test element. A key can be of any shape, regular or irregular, but preferably the shape is such that the key fits into, around or in the vicinity or immediate vicinity of an aperture 23 of a test platform 2 of the present invention that is designed to fit the key and receive the sample. Examples of possible key designs are depicted in FIG. 7.

In some preferred embodiments, a key can be shaped such that a particular sample receiving chamber 1 can be fit into a particular type of test device, or into a particular aperture 23 of a test device, such as a test platform 2. For example, a sample receiving chamber 1 of the present invention can contain one or more reagents that are specific to a particular test for the presence of an analyte of interest. Such a sample receiving chamber 1 can have a key of a shape that fits an analysis device, such as the test platform 2 of the present invention that performs the particular test for the analyte of interest. In one aspect, the key of the sample receiving chamber 1 will not allow the sample receiving chamber 1 to be positioned in an analysis device or test platform 2 that tests for the presence of a different analyte. In other aspects, the key of the sample receiving chamber 1 will allow the sample receiving chamber 1 to be positioned in one or more analysis devices, preferably one or more test platforms 2 with one or more test elements, that test for the presence of one or more analytes.

In another aspect, a test platform 2 can have one or a plurality of test areas designated for different tests. A key can be used to specify where on the test platform 1 a sample receiving chamber 2 with a specific sample, optionally mixed with specific one or more reagents 7, can be inserted or positioned and dispensed for a specific analytical test.

In addition, an analysis device or test platform 2 that can test for the presence, amount, or quality of more than one analyte can have sample application apertures 23 for different tests. An aperture 22 or apertures of a test platform 2 can allow the application of sample, optionally mixed with specific one or more reagents, to specific tests. The aperture 23, or area around or in the vicinity or immediate vicinity of the aperture 23, can be of different shapes wherein the specific shape of the aperture 23, or area around or in the vicinity of the aperture 23, specifies a particular shape of key accepted at that site of a test platform 2 and therefore allows for engagement of a specific sample receiving chamber 1 at that site. For examples see FIG. 8 and FIG. 9. In this way, the user of a particular sample receiving chamber can avoid dispensing sample into a test platform 2 that is not designed, or have the proper test element to test for the analyte of interest, or at an incorrect test site in a test platform 2 having a plurality of tests.

In some preferred embodiments, a key of a sample receiving chamber 1 of the present invention can fit in, on or over a sample application aperture 23, 80 of a test device in only one orientation. For example, the key can be of a shape that has a rounded end and a protruding end, and the sample application aperture 23 is of similar shape, such that the key can engage the analysis device only when the protruding end of the key aligns with the elongated end of the sample application aperture.

A key can comprise any suitable material, but preferably comprises a non-breakable resilient plastic or polymer or copolymer such as polypropylene, polyallomer, polycarbonate or cycloolefins or cycloolefin copolymers. A key can be made by appropriate manufacturing methods, such as injection molding, blow molding, machining or press molding.

Test Platform

Figure 3:
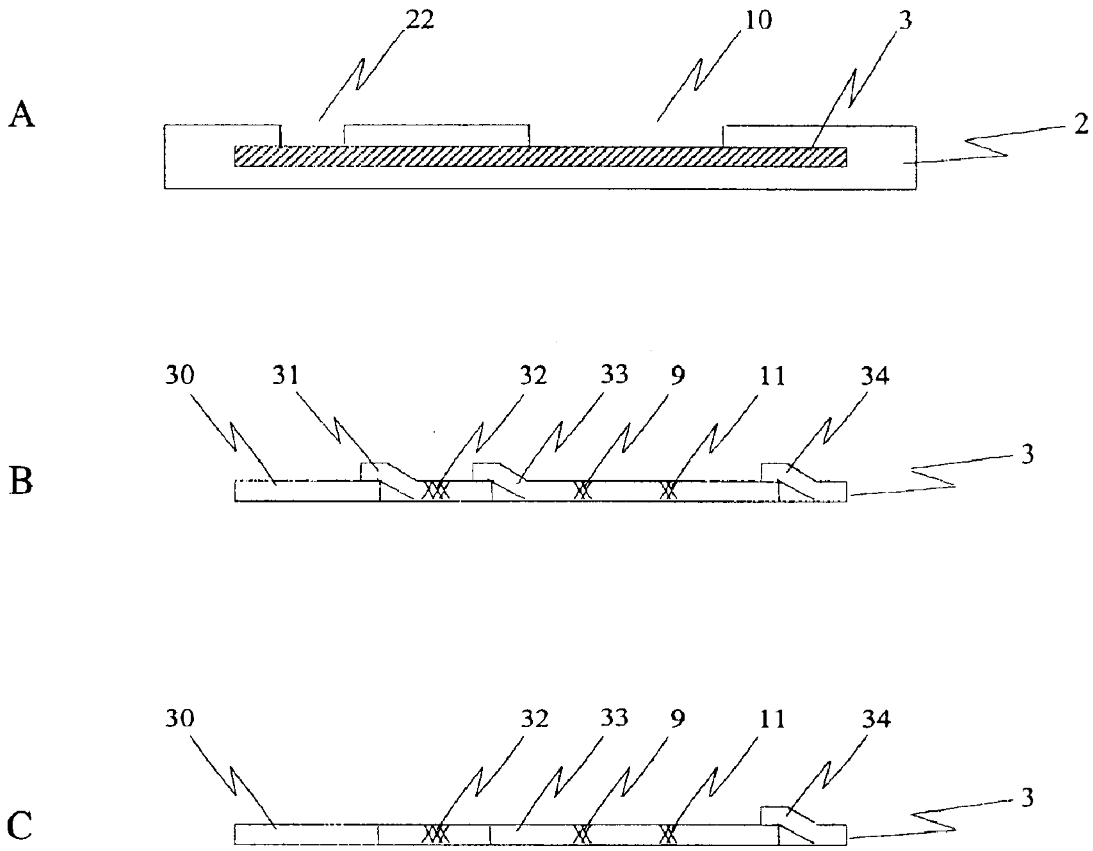
FIG. 3 depicts the test strip, a single strip or a strip comprised of multiple regions in fluid communication, that can be housed within the test platform.

The test platform 2 of the test device of the present invention comprises a housing for one or more test elements such as, but not limited to, a lateral flow detection device such as a test strip 3. For examples see FIG. 3. The test platform 2 can have at least one aperture 22 at which the distal end 21 of a sample receiving chamber 1 can directly or indirectly engage as depicted in FIG. 2. The contents of the sample receiving chamber 1 can be released and flow into the test platform 2 through the aperture 21. Preferably the sample application area 30 of at least one test element is positioned at or near the aperture 21 of the test platform 2 such that the fluid contents of the sample receiving chamber 1 come into fluid contact with the test element.

The test platform 2 of the test device of the present invention can be made of, but not be limited to, any suitable material, such as glass, ceramics, metals, paper, pressed cardboard, or polymers, but preferably comprises a plastic, polymer or copolymer such as those that are resistant to breakage, such as polypropylene, polyallomer, polycarbonate or cycloolefins or cycloolefin copolymers. The test platform 2 can be of any shape or depth but preferably acts as a base to support the sample receiving chamber 1 when engaged with the test platform 2.

In a preferred embodiment of the present invention the test platform 2 can directly or indirectly engage the distal portion of a sample receiving chamber 1 such that the sample receiving chamber 1 is preferably substantially perpendicular to the test platform 2. For examples see FIG. 1 and FIG. 2. The sample receiving chamber 1 can be received into an aperture 22 of the test platform 2 in order to engage the test platform 2. Engagement can be by various structures such as, but not limited to, slide, push, snap, twist, bayonet fit, or screw into the aperture 22. For example, the aperture 22 can have a spiral path along the inner wall and threads can be formed along the external distal region of the sample receiving chamber 1 such that they can be attached by a twisting or screwing motion. In the case of a snap insertion a groove can be formed along the inside wall of the aperture 22 and a raised ridge can encircle the outside distal region of the sample receiving chamber 1 such that the sample receiving chamber 1 can be slid into the aperture 22 and the ridge snaps or locks into the groove of the aperture 22. Alternatively, the aperture 22 can be encircled by a raised edge, with or without grooves or threads, over which the sample receiving chamber 1 can be slid, snapped or screwed to engage the test platform 2. Grooves or threads can be machined into the appropriate component during manufacture using techniques as known in the art. A snap or snug fit can confer a reassuring sound or feel so that the operator is confident that the sample receiving chamber 1 and the test platform 2 have engaged properly.

In another aspect of the test device of the present invention one or more test elements, preferably one or more test strips 3, can be housed by the test platform 2 such that the test elements are made available for use. In one embodiment the test platform 2 has one or more recessed channels or troughs substantially along the top surface of the test platform 2. Preferably the dimensions of such channels or trenches can accommodate a test element, preferably a test strip 3. The one or more channels or trenches can be open 10, that is uncovered, or one or more windows can be positioned to cover the one or more channels or trenches and test elements such that flow and visual results can be observed in accordance with the test and the test element. A window can consist of any transparent material, such as glass, plastic, or mylar, but is preferably break resistant. More preferably the at least one window covering the at least one channel of the test platform 2 is moisture resistant such that the one or more test elements are shielded from external moisture.

In another aspect, the test platform of the present invention can have one or more apertures 22 that can receive a sample or sample and one or more reagents 7 into the test platform. In one embodiment the sample or sample and one or more reagents can be dispensed into an aperture 22 of the test platform 2 from a first device, preferably from a sample receiving chamber 1. In a preferred embodiment the at least one or more apertures 22 are positioned at the end of at least one channel or trench of the test platform 2 having at least one test element. More preferably the one or more apertures 22 can be at the end of the one or more channels or trenches such that a sample application zone 30 of one or more test elements, preferably a test strip 3, is accessible to fluid communication with a sample or sample and one or more reagents (for example see FIG. 3. The one or more channels or trenches can be open, that is uncovered, or one or more windows can be positioned to cover the one or more channels or trenches and test elements such that flow and visual results can be observed in accordance with the test and the test element.

Another embodiment of the present invention can have a test platform 2 with one or more apertures 22 leading to a common sample application region of a test element. Alternatively, a plurality of tests strips 3 with a separate aperture 22 for each, can be housed within a single test platform 2. The test strips can be aligned in parallel (for example see FIG. 9) or be juxtaposed to each other in any pattern. Alternatively a single aperture 22 can be associated with a plurality of test strips. For example, a single sample or sample and reagent can be made available through a single aperture 22 to each of a plurality of test strips such that the single sample can come into fluid communication with the test strips that can test for the presence or absence of different analytes. The plurality of test strips can radiate from the single aperture 22 in all directions or in a confined array, or any combination thereof. A test platform 2 can have one or more apertures that can give access to the sample application region of one or more test strips.

A test strip 3 used in context with the present invention can optionally include indicia that can include a designation for the test to be performed using the test strip 3. Such indicia may be printed on the test strip material using methods known in the art. Alternatively, indicia may be on other thin members, such as plastic or paper, that are attached to the test strip 3, such as by adhesives. A test platform 2 can include one or more test strips including indicia. In the case where a test platform 2 has multiple test strips including indicia, the test strips can include reagents and binding members for different analytes, allowing the user to test for the presence of more than one analyte simultaneously. Test strips having indicia printed directly thereon, or having indicia in the form of attached "sticker labels", can be assembled into test platforms 2 in any of a large number of configurations and combinations, such that a given test device can have a particular subset of test strips specific for the detection of a particular subset of analytes, without changing the design of the test platform 2. In these embodiments, the test platform 2 can include one or more channels or trenches that allows the user to read the indicia on the test strip 3.

In another embodiment of the test platform 2 of the present invention, one or more barrier puncturing devices can be directly or indirectly engaged along the inner wall of the aperture 22 of the test platform 2 such that the barrier puncturing device projects upward from the test platform 2. The projection can be vertical or at an appropriate angle. For example, a sample receiving chamber 1 with a puncturable barrier at or near its distal or outlet end 21 can be inserted into or at an aperture of the test platform 2. The puncturable barrier of the sample receiving chamber 1 can be compromised by the one or more barrier puncturing devices releasing the sample or sample and at least one reagent into the test platform 2. If the one or more barrier puncturing devices are positioned at an angle relative to the barrier to be punctured, a greater amount of damage to the barrier can result, which can provide a greater flow from the sample receiving chamber 1 during the operation of the device of the present invention. The end of the barrier puncturing device, that is poised to puncture a puncturable barrier, can have a variety of structures, preferably those known in weaponry, including but not limited to, pointed, serrated, flat, ovoid, or rounded, all with or without grooves, or can have a sharp edge such as a razor blade, that can rupture the barrier of a sample receiving chamber 1. The puncturing structure can be of any shape including, but not limited to, a lance, spike, spear, arrow, sickle, spade, or blade. A puncturing structure, can be curved and/or connected to the inside wall of the aperture 22 at an angle such that upon puncturing of the barrier by the puncturing structure more surface area of the barrier is disrupted to increase flow of the contents of the sample receiving chamber 1 into the test platform 2.

A puncturing structure can be made to penetrate the barrier in one puncture motion or a circular tear. The puncture is performed by the barrier being penetrated by a puncturing structure at or near a perpendicular angle. Angles different than perpendicular can create greater damage to the barrier. A tearing action on the barrier by the puncturing structure can be accomplished by rotating the sample receiving chamber 1 during engagement to the test platform 2 and the barrier comes in contact with puncturing structure. The puncturing structure can be made to cause additional damage to the barrier by the addition of barbs or other implementations to at least a portion of the puncturing structure. A puncturing structure can be made of any material that is sufficiently rigid and sufficiently sharp at its upper surface such that when forcibly contacted with the barrier of the sample receiving chamber 1, will cause rupture of the barrier of the sample receiving chamber 1. The puncturing structure can be made of one or more materials, such as glass, ceramics, metals, polymers, or the like.

Figure 8:
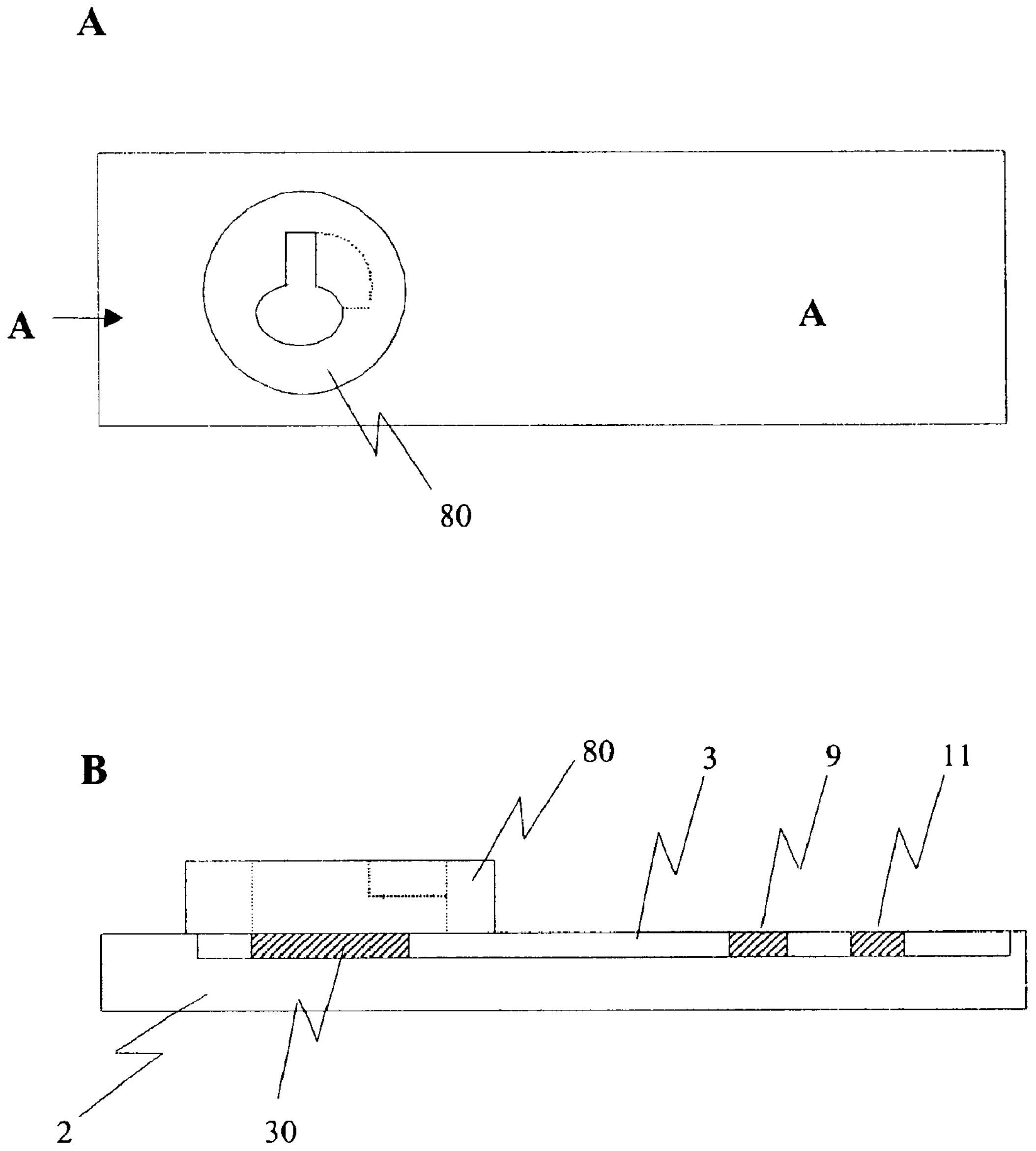
FIG. 8A depicts a top view of an engaging structure 80 on a test platform 2 that can engage a key 71, such as set forth in FIG. 7A. The engaging structure can lock such as by reversibly engaging or irreversibly engaging the key 71 and thus the sample receiving chamber 1. The dashed lines indicate a channel under the surface of the structure that can accept the rotation of the key 71 in FIG. 7A.
FIG. 8B is a cross section view along axis A—A showing the engaging structure 80 and the test platform 2 that includes a test strip 3 that can include a sample application zone 30 and optionally sample detection zone or sample detection zones 9 and optionally control zone or control zones 11 as those terms are known in the art, and as are set forth in commonly assigned U.S. patent application Ser. No. 09/579,673 filed May 26, 2000, which is incorporated herein by reference in its entirety.
Figure 9:
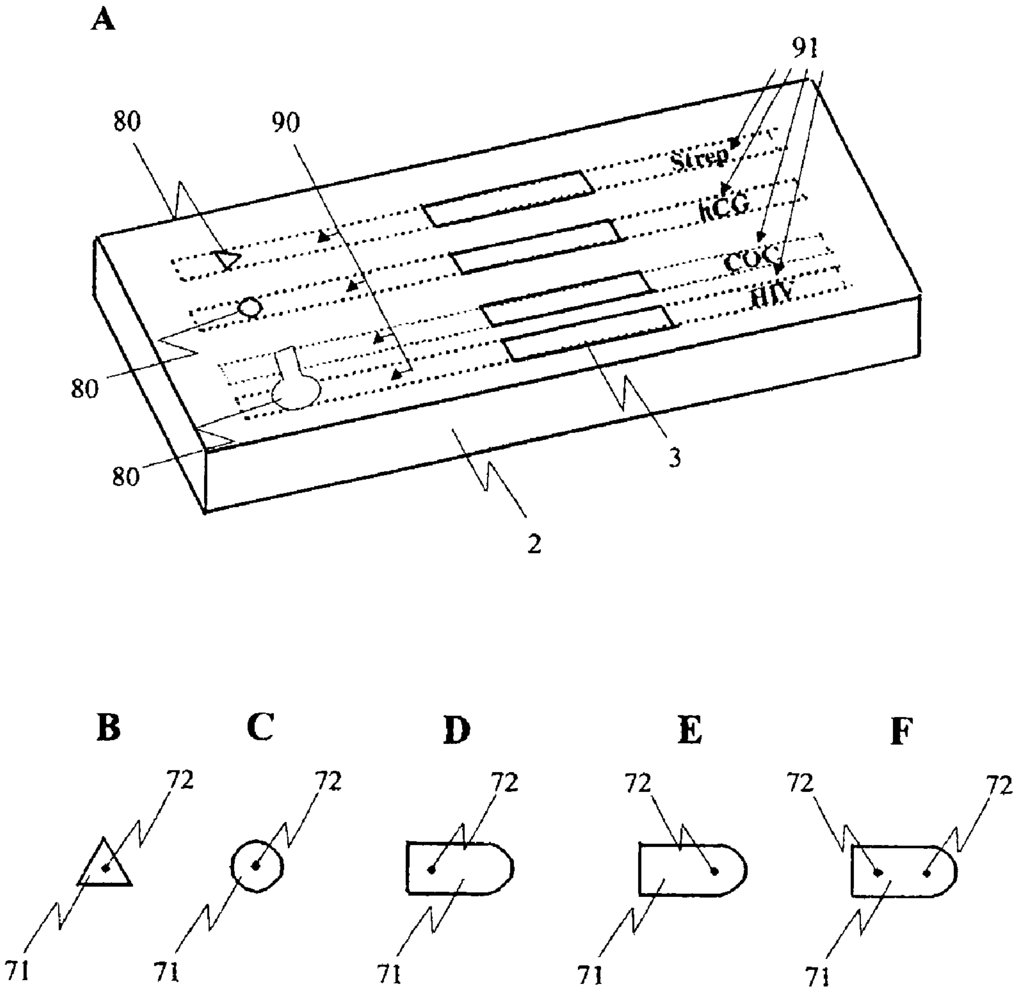
FIG. 9A through FIG. 9F depict a test platform 2 that include one or more engaging structures 80 that can engage one or more keys 71 of sample receiving chamber of the present invention. The test platform 2 in this instance is a multi-channel test device that includes a plurality of test strips 90 for a variety of analytes, such as Strep (*Streptococcus*), hCG (human chorionicgonadotropin), COC (cocaine) and HIV (human immunodeficiency virus) as depicted by surface indicia 91, thus including tests for etiological agents, pregnancy and drugs of abuse.

In another aspect of the present invention the one or more apertures 22 of the test platform 2 can be shaped to receive a key that can be used to orient and/or engage a sample receiving chamber 1 For example see FIG. 8. In one embodiment one or more apertures 22 of a test platform 2 can be designed to accept a key engaged at the distal end of a sample receiving chamber 1 of the present invention. In some preferred embodiments, a key can be shaped such that the distal end of a particular sample receiving chamber 1 can be fit into or at a single aperture 23 or a particular aperture 23 of at least one of several apertures of a test platform 2 as depicted in FIG. 9. For example, a sample receiving chamber 1 of the present invention can contain a sample with one or more reagents that are specific to a particular test for the presence of an analyte of interest. Such a sample receiving chamber 1 can have a key of a shape that fits an aperture 23 of a test platform 2 housing a specific test element that performs the particular test for an analyte of interest. In one aspect the key of the sample receiving chamber 1 will not allow the sample receiving chamber 1 to be positioned in the aperture 23 of a test platform 2 that links to a test element that test for the presence of a different analyte. In other aspects, the key of the sample receiving chamber 1 will allow the sample receiving chamber 1 to be positioned in apertures 23 of one or more test platforms 2 that links to one or more test elements that test for the presence of one or more analytes. In this case, one or more reagents mixed or supplied with a sample receiving chamber 1 can be compatible with more than one test for more than one analyte.

Test Element

The test element housed within the test platform 2 of the test device of the present invention can be of any test element known in the art and preferably comprises a lateral flow detection device such as a test strip 3, preferably an immunological test strip. (For examples see FIG. 3.) The test platform 2 of the present invention can house one or more test strips. The one or more test strips can be of any shape and dimensions, but preferably is a rectangular test strip 3.

The test strip 3 of a test device of the present invention may comprise, at least in part, any bibulous or non-bibulous material, such as nylon, paper, glass fiber, dacron, polyester, nitrocellulose, polyethylene, olefin, or other thermoplastic materials such as polyvinyl chloride, polyvinyl acetate, copolymers of vinyl acetate and vinyl chloride, polyamide, polycarbonate, polystyrene, etc. In a preferred embodiment, at least one test strip 3 material is nitrocellulose having a pore size of at least about 1 micron, more preferably of greater than about 5 microns, or about 8–12 microns. Very suitable nitrocellulose sheets having a nominal pore size of up to approximately 12 microns, are available commercially from, for example, Schleicher and Schuell GmbH.

A test strip 3 can include one or more materials. If a test strip 3 comprises more than one material, the one or more materials are preferably in fluid communication as depicted in FIG. 3B and FIG. 3C. One material of a test strip 3 may be overlaid on another material of the test strip, such as for example, filter paper overlaid on nitrocellulose. Alternatively or in addition, a test strip 3 may include a region comprising one or more materials followed by a region comprising one or more different materials. In this case, the regions are in fluid communication and may or may not partially overlap one another.

The material or materials of the test strip 3 can be bound to a support or solid surface such as found, for example, in thin-layer chromatography and may have an absorbent pad either as an integral part or in liquid contact. For example, a test strip 3 may comprise nitrocellulose sheet "backed", for example with a supporting sheet, such as a plastic sheet, to increase its handling strength. This can be manufactured by forming a thin layer of nitrocellulose on a sheet of backing material. The actual pore size of the nitrocellulose when backed in this manner will tend to be lower than that of the corresponding unbacked material. Alternatively, a preformed sheet of nitrocellulose and/or one or more other bibulous or non-bibulous materials can be attached to at least one supporting sheet, such as a sheet made of polymers (see, U.S. Pat. No. 5,656,503 to May et al., issued Aug. 12, 1997). The supporting sheet can be transparent, translucent or opaque. In the aspect of the present invention where the support sheet is transparent, the supporting sheet is preferably moisture impervious but can be moisture resistant or moisture pervious. The test strip 3 can be assembled in a test platform 2 of the present invention such that the support sheet is optionally on the side of the test strip 2 that can be viewed from the upper face of the test platform 2. In this way the test strip 2 can be viewed along an open 10 or uncovered channel of the test platform 2, and the test strip 3 is protected from contact with moisture. In another embodiment of the present invention the test strip 3 can be viewed through a window comprised of a transparent material such as glass, plastic, or mylar, but preferably break resistant.

In the following discussion strips of test strip 3 material will be described by way of illustration and not limitation.

Generally, test strips 3 of a test device of the present invention include a sample application zone 30 and a test results determination region 33. The test results determination region 33 can include either or both of one of more analyte detection zones 9 and one or more control zones 111. Optionally, a test strip 3 can include a reagent zone 32.

One or more specific binding members in the test results determination region 33 of the test strip 3 can be impregnated throughout the thickness of the bibulous or non-bibulous material in the test results determination region 33 (for example, specific binding members for one or more analytes can be impregnated throughout the thickness of the test strip material in one or more analyte detection zones 9, and specific binding members for one or more control analytes can be impregnated throughout the thickness of the test strip material in one or more control zones 11, but that need not be the case). Such impregnation can enhance the extent to which the immobilized reagent can capture an analyte present in the migrating sample. Alternatively, reagents, including specific binding members and components of signal producing systems may be applied to the surface of the bibulous or non-bibulous material. Impregnation of specific binding members into test strip materials or application of specific binding members onto test strip materials may be done manually or by machine.

Nitrocellulose has the advantage that a specific binding member in the test results determination zone 9 can be immobilized without prior chemical treatment. If the porous solid phase material comprises paper, for example, the immobilization of the antibody in the test results determination zone 9 can be performed by chemical coupling using, for example, CNBr, carbonyldiimidazole, or tresyl chloride.

Following the application of a specific binding member to the test results determination zone, the remainder of the porous solid phase material should be treated to block any remaining binding sites elsewhere. Blocking can be achieved by treatment with protein (for example bovine serum albumin or milk protein), or with polyvinylalcohol or ethanolamine, or any combination of these agents. A labeled reagent for the reagent zone 32 can then be dispensed onto the dry carrier and Will become mobile in the carrier when in the moist state. Between each of these various process steps (sensitization, application of unlabeled reagent, blocking and application of labeled reagent), the porous solid phase material should be dried.

To assist the free mobility of the labeled reagent when the test strip is moistened with the sample, the labeled reagent can be applied to the bibulous or non-bibulous material as a surface layer, rather than being impregnated in the thickness of the bibulous material. This can minimize interaction between the bibulous or non-bibulous material and the labeled reagent. For example, the bibulous or non-bibulous material can be pre-treated with a glazing material in the region to which the labeled reagent is to be applied. Glazing can be achieved, for example, by depositing an aqueous sugar or cellulose solution, for example of sucrose or lactose, on the carrier at the relevant portion, and drying (see, U.S. Pat. No. 5,656,503 to May et al., issued Aug. 12, 1997). The labeled reagent can then be applied to the glazed portion. The remainder of the carrier material should not be glazed.

The reagents can be applied to the carrier material in a variety of ways. Various "printing" techniques have previously been proposed for application of liquid reagents to carriers, for example micro-syringes, pens using metered pumps, direct printing and ink-jet printing, and any of these techniques can be used in the present context. To facilitate manufacture, the carrier (for example sheet) can be treated with the reagents and then subdivided into smaller portions (for example small narrow strips each embodying the required reagent-containing zones) to provide a plurality of identical carrier units.

In embodiments where the analyte is detected by a signal producing system, such as by one or more enzymes that specifically react with the analyte, one or more components of the signal producing system can be bound to the analyte detection zone 9 of the test strip material in the same manner as specific binding members are bound to the test strip material, as described above. Alternatively or in addition, components of the signal producing system that are included in the sample application zone 30, the reagent zone 32, or the analyte detection zone 9 of the test strip 3, or that are included throughout the test strip 3, may be impregnated into one or more materials of the test strip 3. This can be achieved either by surface application of solutions of such components or by immersion of the one or more test strip materials into solutions of such components. Following one or more applications or one or more immersions, the test strip material is dried. Alternatively or in addition, components of the signal producing system that are included in the sample application zone 30, the reagent zone 32, or the analyte detection zone of the test strip 9, or that are included throughout the test strip 3, may be applied to the surface of one or more test strip materials of the test strip 3 as was described for labeled reagents.

Sample Application Zone

The sample application zone 30 is an area of a test strip 3 where a sample, such as a fluid sample, such as a biological fluid sample such as blood, serum, saliva, or urine, or a fluid derived from a biological sample, such as a throat or genital swab, is applied. The sample application zone 30 can include a bibulous or non-bibulous material, such as filter paper, nitrocellulose, glass fibers, polyester or other appropriate materials. One or more materials of the sample application zone 30 may perform a filtering function, such that large particles or cells are prevented from moving through the test strip 3. The sample application zone 30 can be in direct or indirect fluid communication with the remainder of the test strip 3, including the test results determination zone 9. The direct or indirect fluid communication can be, for example, end-to-end communication as depicted in FIG. 3C, overlap communication as depicted in FIG. 3B and FIG. 3C, or overlap or end-to-end communication that involves another element, such as a fluid communication structure such as filter paper.

The sample application zone 30 can also include compounds or molecules that may be necessary or desirable for optimal performance of the test, for example, buffers, stabilizers, surfactants, salts, reducing agents, or enzymes.

Reagent Zone

The test strip 3 can also include a reagent zone 32 where reagents useful in the detection of an analyte can be provided immobilized (covalent or non-covalent immobilization) or not immobilized, particularly when in a fluid state. The reagent zone 32 can be on a reagent pad, a separate segment of bibulous or non-bibulous material included on the test strip 3, or it can be a region of a bibulous or non-bibulous material of a test strip 3 that also includes other zones, such as an analyte detection zone 9. In one aspect of the invention, the reagent zone 32 can include a labeled specific binding member, such as antibodies or active fragments thereof attached or linked to a label. Such labeled specific binding members can be made using methods known in the art. The specific binding members can bind an analyte and/or can bind a control compound.

In one preferred example involving detection of hCG, the reagent zone 32 includes two populations of colored beads. One population of colored beads is attached to an anti-rabbit IgG antibody or active fragment thereof and the other population of colored beads is attached to an anti-hCG beta chain antibody or active fragment thereof. The labeled anti-rabbit IgG antibody or antibody fragment is used for visual detection of a signal in the control zone 11 of the test strip 9. A color signal in the control zone 11 indicated that the sample has passed through the detection zone 9. The labeled anti-hCG beta chain antibody or fragment thereof provides a visual signal in the detection zone 9 indicating the presence of hCG in the sample.

Other preferred embodiments are having anti-(drug of abuse) antibodies or active fragments thereof bound to a population of colored beads. More than one population of beads can be used as in the forgoing example to provide a visual signal in the detection zone 9 and a second visual signal in the control zone 9. The two populations of beads can be the same or different colors or be provided as a mixture of colors. Alternatively or in addition, different populations of beads bound to different antibodies or antibody fragments can be used to indicate the presence of more than one analyte in a sample by producing one or more visual signals in one or more detection zones 9.

In another aspect of the invention, the reagent zone 32 includes the analyte or an analyte analog bound to a population of colored beads. In this case, the analyte in the sample competes with the labeled analyte or analyte analog provided in the reagent zone 32 for binding to a specific binding member in the test results determination zone. A reduced visual signal in comparison with a control sample lacking analyte indicates the presence of analyte in the sample. More than one population of beads can be used as in the forgoing examples to provide a visual signal in the analyte detection zone 9 and a second visual signal in the control zone 11. Alternatively or in addition, different populations of beads bound to different analytes or analyte analogs can be used to indicate the presence of more than one analyte in a sample by producing one or more visual signals in one or more detection zones 9.

Preferred labels are beads such as metal particles, such as gold, or polymeric beads, such as colored beads, or particles of carbon black. Other labels include, for example, enzymes, chromophores or fluorophores such as they are known in the art, particularly in immunoassays, or later developed. The populations of beads are provided in powdered form on the reagent zone 32, which can include a bibulous material, such as filter paper, glass fibers, nylon, or nitrocellulose. These reagents are reversibly bound to the reagent zone 32 because they can be mobilized when placed in contact with a fluid, such as a fluid sample passing along a test strip 3.

In another embodiment of the invention, the reagent zone 32 can include components of a signal producing system, for example, catalysts, such as enzymes, cofactors, electron donors or acceptors, and/or indicator compounds.

The reagent zone 32 can also include compounds or molecules that may be necessary or desirable for optimal performance of the test, for example, buffers, stabilizers, surfactants, salts, reducing agents, or enzymes.

Test Results Determination Zone

The test results determination zone includes immobilized or not immobilized reagents that can detect the presence of the analyte being tested for, such as but not limited to, drugs of abuse, hormones, metabolites, and antibodies. Such reagents are preferably in a dry state and can be covalently immobilized, non-covalently immobilized, or not immobilized in a fluid state. The test result determination zone can include either or both of one or more analyte detection zones 9 and one or more control zones 11.

Depending on the particular format and analyte being tested for, a variety of reagents can be provided at the test results determination zone. For example, the test results determination zone can include specific binding members such as antibodies, enzymes, enzymatic substrates, coenzymes, enhancers, second enzymes, activators, cofactors, inhibitors, scavengers, metal ions, and the like. One or more of the reagents provided at the test results determination zone can be bound to the test strip material. Test strips 3 including such reagents are known in the art and can be adapted to the test device of the present invention.

In a preferred aspect of the present invention, the one or more analyte detection zones 9 of the test results determination zone include one or more immobilized (covalently or non-covalently immobilized) specific binding members that bind with one or more analytes of interest, such as one or more drugs, hormones, antibodies, metabolites, or infectious agents, when the analytes are also bound by specific binding members bound to a label as are provided in the reagent zone 32. Thus, in embodiments where the reagent zone 32 contains one or more specific binding members for the analyte, the specific binding members of the reagent zone 32 and analyte detection zone 9 should bind with different epitopes on the analyte being tested for. For example, when a labeled specific binding member in the reagent zone 32 binds with the beta-chain of hCG, then the immobilized specific binding member in the analyte detection zone 9 should bind with another area of hCG, such as the alpha-chain of hCG. Thus, when hCG is present in the sample, the hCG will bind the labeled anti-beta hCG which carried along to the test result determination zone at the analyte detection zone 9 which binds with the immobilized anti-alpha hCG to provide a visual readout at that locus.

The analyte detection zone 9 can include substrates which change in an optical property (such as color, chemiluminescence or fluorescence) when an analyte is present. Such substrates are known in the art, such as, but not limited to, 1,2-phenylenediamine, 5-aminosalicylic acid, 3,3',5,5'tetra methyl benzidine, or tolidine for peroxidase; 5-bromo-4-chloror-3-indolyl phosphate/nitroblue tetrazolium for alkaline phosphatase and 5-bromo-4-chloro-3-indolyl-beta-D-galactopyranoside, o-nitrophenyl-beta-D-galactopyranoside, napthol-AS-BI-beta-Dgalactopyranoside, and 4-methyl-umbelliferyl-beta-D-galactopyranoside for beta galactosidase.

In embodiments where an analyte is detected by a signal producing system, one or more components of the signal producing system, such as enzymes, substrates, and/or indicators, can be provided in the analyte detection zone 9. Alternatively, the components of the signal producing system can be provided elsewhere in the test strip 3 and can migrate to the analyte detection zone 9.

Optionally, the test results determination zone can include a control zone 11. The control zone 11 can be upstream from, downstream from, or integral with the analyte detection zone 9 of the test result determination zone. In the latter case, when analyte and control give a positive reaction, the control zone 11 and analyte detection zone 9 can form an indicia, such as a "+" sign for a positive reaction and a "−" sign for a negative reaction based on the particular format of the assay.

The control zone 11 provides a result that indicates that the test on the test strip 3 has performed correctly. In one preferred aspect of the present invention, the reagent zone 32 includes a specific binding member that binds with a known analyte different from the analyte being tested for. For example, a rabbit-IgG may be provided in the reagent zone 32. The control zone 11 can include immobilized (covalently or non-covalently) anti-rabbit-IgG antibody. In operation, when the labeled rabbit-IgG in the reagent zone 32 is carried to the test result determination zone and the control zone 11 therein, the labeled rabbit-IgG will bind with the immobilized an anti-rabbit-IgG and form a detectable signal.

The control zone 11 can include substrates which change in an optical property (such as color, chemiluminescence or fluorescence) when a control substance is present.

In one aspect of the present invention, a test strip 3 can include an adulteration control zone that is capable of detecting an adulteration analyte or an adulteration indicator. Such an adulteration control zone can be in addition to or in place of a control zone 11 or a test results determination zone 9 as described herein. In one aspect of the present invention, the test strip 3 can include an adulteration control zone and a control zone 11 and can optionally detect another analyte such as a drug. In the case where a test strip 3 includes an adulteration control zone and a control zone 11, but does not detect another analyte, the test strip 3 can be used as a separate control strip, which can be provided in a separate channel of a the test platform 2 of the present invention.

The adulteration control zone can detect an analyte using any appropriate method, such as specific binding methods or using chemical detection methods. These types of detection methods are known in the art and are described herein. For example, specific binding methods such as antibody detection methods are described herein. Also, methods to detect an analyte using signal detection methods using chemical or enzymatic methods are also described herein.

Adulteration control zones preferably detect the presence or amount of an analyte that reflects sample adulteration, such as adulteration by dilution, such as substitution or addition of materials from another species, subject or non-human source to a sample or by the addition of an altering agent. Depending on the monitoring of sample acquisition, sample chain of custody and sample preparation, the need for adulteration controls can be different. For example, blood, serum or plasma samples tend to be more difficult for a subject from which such a sample is taken from to adulterate because such samples tend to be drawn by a phlebotomist or other health-care professional and the chain of custody for such samples tend to be relatively rigorous. On the other hand, samples of urine or other bodily fluids tend to be less stringently controlled, but that need not be the case. The choice of adulteration controls can be chosen based on the particular circumstances for sample collection and chain of title as appropriate.

An appropriate adulteration control for different sample types, such as serum, blood, saliva or urine, can be chosen by the skilled artisan. For example, preferred analytes for blood or blood derived sample dilution include but are not limited to hematocrit, protein concentration, hemoglobin (particularly for red blood cell lysis) and analytes for urine or urine derived sample dilution include but are not limited to creatine. Preferred analytes for blood or blood derived sample species include but are not limited to cell-surface antigens or immunoglobulins of any class or subclass, such as IgG, IgM, IgA, IgE or IgD and and analytes for urine or urine derived sample species include but are not limited to cell-surface antigens or immunoglobulins of any class or subclass, such as IgG, IgM, IgA, IgE or IgD and analytes for urine or urine derived sample subject include but are not limited to hormones such as testosterone, estrogen or cell surface antigens. Preferred analytes for adulterants for blood or blood derived samples include but are not limited to pH, hemoglobin and nitrites. Preferred analytes for adulterants include, but are not limited to pH and the adulterants or their derivatives, such as break down products, or derivatives in the sample based on the action of the adulterant, such as the presence or absence of analytes normally present in the sample in the absence of an adulterant or break down products or altered analytes based on the action of an adulterant. Preferred adulterants include, but are not limited to hypochlorite (bleach), chlorine, gluteraldehyde, soap, detergent, Drano (TM), Visine (TM), Golden Seal Tea (TM), citrus products such as juice such as lemon or lime juice, nitrate, Urine Luck (TM) and pyridinium chlorochromate.

Adulteration control zones can be made using methods known in the art and described herein, such as for making a test results determination zone to detect an analyte. The adulteration control zone can be thought of as a test results determination zone for an adulteration analyte and thus the reagent zone can include appropriate reagents for performing an assay for an adulteration analyte. For example, a test strip 3 can include detectably labeled rabbit anti-human IgG and the adulteration control zone can include immobilized goat anti-human IgG antibodies. Thus, in operation of the test strip 3, the sample adulteration control zone having the detectable label bound thereto would indicate that the sample contains human IgG and thus is presumptively of human origin. If, for example, a supposedly human serum sample was used as a sample in such a test strip 3, the lack of a detectable label in the sample adulteration control zone would indicate that the sample was not of human origin and thus would not be a valid test. In those circumstances, the test results would indicate that the sample was adulterated, such as providing a serum sample from another species or by altering the sample such that human IgG was degraded or otherwise not present. Adulteration tests can be quantitative or semi-quantitative such that dilution of a sample of human origin would result in a readout having less detectable label than a standard range for undiluted samples. Adulteration tests can be used to detect one or more adulterants in one or more test strips. For example, a single adulteration test strip can detect one or more adulterants.

In one preferred aspect of the present invention, the test strip 3 can include a results determination zone that includes a control zone 11 and a analyte detection zone 9, and a sample adulteration control zone. In another aspect of the present invention, a test strip 3 can include a results determination zone that optionally includes a control zone 11, and optionally an adulteration control zone. A second test strip 3 can include an adulteration control zone and optionally a control zone 11. Preferably, this second test strip 3 includes both an adulteration control zone and a control zone 11, but that need not be the case. In the instance where one or more first test strips can be used to detect an analyte other than an adulteration analyte and one or more second test strips can be used to detect an adulteration analyte, the test strips can be provided in a single test platform 2 of the present invention, such as a multi-channel test platform 2.

Orientation of Zones

The various zones of a test strip 3, including a sample application zone 30, one or more reagent zones 32, and one or more test result determination zones, including one or more analyte detection zones 9 and optionally including one or more control zones 11 and one or more adulteration zones, can be on a single strip of material, such as filter paper or nitrocellulose, or can be provided on separate pieces of material. The different zones can be made of the same or different material or a combination of materials, but preferably are selected from bibulous materials, such as filter paper, fiberglass mesh and nitrocellulose. The sample application zone 30 preferably includes glass fibers, polyester or filter paper, the one or more reagent zones 32 preferably include glass fibers, polyester or filter paper and the test results determination zone, including one or more analyte detection zones 9 and optionally including one or more control zones 11, preferably include nitrocellulose.

Optionally, a fluid absorbing zone is included. The fluid absorbing zone preferably includes absorbant paper and is used to absorb fluid in a sample to drive fluid from the sample application zone 30 through the reagent zone 32 and the detection zone.

Preferably, the zones are arranged as follows: sample application zone 30, one or more reagent zones 32, one or more test results determination zones, one or more control zones 11, one or more adulteration zones, and fluid absorbing zone. If the test results determination zone includes a control zone 11, preferably it follows the analyte detection zone 9 of the test result determination zone. All of these zones, or combinations thereof, can be provided in a single strip of a single material. Alternatively, the zones are made of different materials and are linked together in fluid communication. For example, the different zones can be in direct or indirect fluid communication. In this instance, the different zones can be jointed end-to-end to be in fluid communication (for example see FIG. 3C), overlapped to be in fluid communication (for example see FIG. 3B), or be communicated by another member, such an joining material, which is preferably bibulous such as filter paper, fiberglass or nitrocellulose. In using a joining material, a joining material may communicate fluid from end-to-end joined zones or materials including such zones, end-to-end joined zones or materials including such zones that are not in fluid communication, or join zones or materials that include such zones that are overlapped (such as but not limited to from top to bottom) but not in fluid communication.

When and if a test strip 3 includes an adulteration control zone, the adulteration control zone can be placed before or after the results determination zone. When a control zone 11 is present in the results determination zone on such a test strip 3, then the adulteration control zone is preferably before the control zone, but that need not be the case. In the aspect of the present invention where a test strip is a control test strip for the determination of an adulteration analyte and/or a control, then the adulteration control zone can be placed before or after the control zone, but is preferably before the control zone.

Fluid Communication

In a preferred aspect of the test device of the present invention the sample receiving chamber 1 with sample or sample and one or more reagents is engaged with the test element such that the distal, or outlet end 21 of the sample receiving chamber 1 is inserted or otherwise affixed to or within an aperture 22 of the test platform 2. The contents of the sample receiving chamber 1 can be released into the aperture 22 of the test platform 3 and comes into fluid contact with at least one test element, preferably the sample application zone of a test strip 3. The sample or sample and one or more reagents flow along the test strip by wicking action and can optionally come into fluid contact with specific one or more anlyte, antibody or labeled member for an analyte, or a combination thereof, which can be freely mobile within the bibulous material when in the moist state. In a preferred aspect of the present invention the test contents of the sample or sample and one or more reagents and optional elements of the test strip 3 come into fluid contact with a detection zone of the test strip that can indicate the presence or absence for a specific analyte in the sample.

II A method of Detecting an Analyte in a Sample

The methods disclosed herein may be performed using a variety of test device configurations as previously described and as setforth in the disclosed methods and examples. The device of the present invention can be used to collect a sample, transfer the sample to a sample receiving chamber 1 and optionally mix the sample with one or more reagents 7. The sample or sample and one or more reagents can then be conducted to a test element within a test platform 2 to detect one or more analytes in the sample, preferably a sample application zone 30 of a test strip 3. The sample can be gaseous, liquid, colloidal or solid. Examples of liquid or fluid samples that can be inserted into the sample receiving chamber 1 of the present embodiment can include water including pond, lake, stream, or "runoff" water, or biological samples such as blood, serum, saliva, or urine. Other biological samples can include fecal samples, and throat or genital swabs. Examples of solid samples can include such materials as dirt, grains, granules, powders or pellets.

To collect a sample into the sample receiving chamber 1 a fluid or colloidal sample can be inserted via various techniques, for example pipeting, pouring or by use of a dropper. Alternatively a sample collection device can be used to collect a sample and transfer the sample into the sample receiving chamber 1. The sample collection device can be of different structures but is preferably a swab 4. The swab 4 can be used to collect the sample onto the swab head 5 by different embodiments such as for example dipping, swiping or swabbing. The swab 4 with sample can be inserted into the sample receiving chamber 1 that can optionally contain one or more reagents or can have one or more reagents 7 added to the sample receiving chamber 1 during or after insertion of the sample collection device and sample. In each scenario the sample can be mixed or otherwise extracted into the sample receiving chamber 1 by an extraction solution that can include, for example, the one or more diluents, buffers or reagents. Optionally, one or more structures, for example one or more ribs or edges 51 located longitudinally within the inner wall of the sample collection device can facilitate extraction of the sample from a swab 4 by rotating the swab 4 such the one or more ribs or edges 51 and the one or more spaces in-between alternatively compress and decompress different portions of the swab head 5 to release sample into the sample receiving device.

The sample receiving chamber 1 can be integrally affixed to or at an aperture 22 of a test platform 2 or can be separate from the test platform 2 and can be optionally engaged to an aperture 22 of the test platform 2. In each instance the sample receiving chamber 1 is in a vertical position and essentially perpendicular to the test platform 2. When separate, the sample collection device and sample and optional one or more reagents, can be added to the sample receiving chamber 1 before or after the sample receiving chamber 1 is engaged with the test platform 2.

The sample receiving chamber 1 can be engaged to the test platform 2 by various techniques, for example the sample receiving chamber 1 can be slid, screwed or snapped into an aperture 22 of the test platform 2. Optionally, the sample receiving chamber 1 can be oriented and locked into position with the test platform 2 using a key structure. The user positions the distal end of the sample receiving chamber 1 into an aperture 23 of the test platform 2 such that the key fits into an aperture 23 designed to receive the key, and optionally locks the sample receiving chamber 1 into place. Alternatively an aperture 22 of the test platform 2 can be encircled by a raised edge, with or without grooves or threads, over which the sample receiving chamber 1 can be slid or snapped or screwed onto the raised edge.

The contents of the sample receiving chamber 1 can be contained and allowed to mix or incubate for a specific amount of time. To allow for containment and incubation the mixture can be prevented from flowing out of the distal end (the end that engages the test platform) of the sample receiving chamber 1 by a mechanical structure, for example a closed valve 20, or a physical structure, for example a membrane. Flow of the contents of the sample receiving chamber 1 can be released in a regulated fashion into an aperture 22 of the test platform 2 by opening, fully or partially, a valve 20 at the distal end of the sample receiving chamber. The valve can be of any type known in the art. For example a valve can align, or partially align, openings by a twisting or sliding mechanism, or by a stopcock (for examples see FIG. 4), whereby the contents can be released from the sample receiving chamber 1 in a controlled or regulated manner.

Alternatively, when separate from the test platform 2, a puncturable membrane can be located at or near the distal end of the sample receiving chamber. In this instance a membrane rupturing or puncturing device can be directly or indirectly engaged within or near the aperture 22 of the test platform 2. The user dispenses the sample or sample and reagent or reagents into the test platform 2 by inserting the distal or outlet end 21 of the sample receiving chamber 1 into an aperture 22 of the test device. The user can insert, by sliding, twisting or screwing the sample receiving chamber 1 into an aperture 22 having a membrane rupturing or puncturing device. The membrane can be punctured or torn by the membrane puncturing or rupturing device thereby releasing the contents of the sample receiving chamber 1 through the aperture 22 and into the test platform 2. Optionally, a filtering device can be located within the sample receiving chamber 1 whereby, upon release of the contents by opening a valve, or rupturing a membrane, the filter can filter out unwanted aggregates or particulates from the sample or sample and reagent or reagents entering the test platform 2.

The test platform 2 of the present invention can house a test element, preferably an immunological test strip 3. Thereby the test device of the present invention can be used to determine whether a specific analyte is present in a sample. The analyte of interest can be of various kinds, for example a biological moiety, for example a antibody or surface antigen or a hormone such as hCG (human chorionicgonadotropin); a drug or chemical moiety; or an etiological agent or extract from an etiological agent such as Strep (*Streptococcus*) or HIV (human immunodeficiency virus). The sample application zone 30 of one or more test strips 3 can be positioned immediately below or in the vicinity of an aperture 22 of the test platform 2. The user can release the contents of the sample receiving chamber 1, optionally in a controlled or actuated manner, and onto the sample application zone 30 of the one or more test strips 3. The sample and sample and reagent travels by capillary flow along the immunochromatographic test strip 3 and dependent on the test strip 3 used the presence or absence of an analyte in the sample can be determined by the presence or absence of a visual line in the detection zone 9 of a test strip 3 as viewed through an opening 10 or window on the test platform 2.

III In Line Test Device with O-Ring Valve Actuating Mechanism

This embodiment of the present invention includes a test device that includes a sample receiving chamber 101 and a test platform 120 that preferably include a test element. The sample receiving chamber 101 preferably engages the test platform 120. The sample receiving chamber includes a male insert 102 with a stud 103 that protrudes from the side wall of the cylinder shaft of the male insert 102. The female receptor 111 has an open groove guide 114 that is situated along the side of the female receptor 111. The open groove guide 114 of the female receptor 111 engages and guides the stud 103 of the male insert 102 to acuate the o-ring 108 valve structure. To actuate the sample receiving chamber 101 o-ring 108 valve structure, an operator can rotate the grooved ridge 105 at the proximal 109 end of the male insert 102. The content of the sample receiving chamber 101, when engaged with the test platform 120, can be released into the test platform and onto the test element by an o-ring 108 twist valve by aligning the male outlet port 106 of the male insert 102 with the female outlet port 115 of the female receptor 111. The internal incline 104 on the male insert 102 of the male insert 102 to guide the flow of the content inside the sample receiving chamber to the male outlet port 106 of the male insert 102. The internal longitudinal ribs 107 of the male insert 102 allows a swab or brush that is used to collect specimens release the specimens into the sample receiving chamber by the rotation of the swab or brush against the internal longitudinal ribs 107 of the male insert 102. The o-ring 108 is seated around the male outlet port 106 of the male insert 102 to prevent leakage and allow for a smooth glide when the grooved ridge 105 of the male insert 102 is rotated for release of the content of the sample receiving chamber. The female receptor 111 is a tube like structure with a base 112 that can be engaged to the test platform 120. The base 112 of the female receptor 111 has a notch 113 for proper attachment with the stud 135 of the engaging structure 132 of the top portion 131 of the test platform 120. The test platform 120 houses one or more test elements. The top portion 131 of the test platform is attached to the bottom portion 121 of the test platform 120 by on or more snap lock mechanisms 136 of the top portion 131. The top portion 131 and one or more snap lock mechanisms 123 of the bottom portion 121 of the test platform 120. The bottom portion includes one or more support structures 122 for supporting the test element. The top portion 131 of the test platform 120 includes a test result window 133 through which the result of the test can be viewed. The test platform 120 includes one or more vent holes 134 to allow any trapped air or gas that may result from the testing to escape from the inside of the test platform 120.

EXAMPLES

The examples provided may be performed using a variety of test device configurations as previously described and setforth.

Example 1

Method of Using Device for Disease Detection: Strep-A

A throat specimen is obtained from a patient exhibiting signs and symptoms of pharyngitis using a standard size rayon or dacron swab. The tonsil area of the throat is swabbed. The sample receiving chamber of the test device is seated on the test platform housing a lateral flow test strip device. Four drops or approximately 160 microliters of Reagent A (2 molar sodium nitrate) and four drops, approximately 160 microliters of Reagent B (0.2 molar acetic acid), are added to the extraction device. The swab containing the throat specimen is inserted into the sample receiving chamber and rotated in a back and forth motion for about 10 seconds. The swab is then allowed to incubate in this solution for 60 seconds. After this time has elapsed the valve structure is actuated, with the swab still remaining in the sample receiving chamber. The liquid contents of the sample receiving chamber, equal to approximately 200 micoliters, is transferred to the sample pad of the test device configured to detect Strep-A antigen. Sample flow is initiated on the test device by capillary action and the result of the test is viewed through the test result window 5 minutes after actuating the extraction device valve.

Example 2

Method of Using Device for Disease Detection: Chlamydia

Endocervical specimens is collected using either rayon or dacron swabs with plastic shafts or a cytobrush. A key structure on a sample receiving chamber of the test device is locked into the corresponding key receptor located on the test platform housing a lateral flow test strip device. One hundred and fifty (150) microliters of 1 normal potassium hydroxide is placed into the sample receiving chamber of the device. The swab or brush is placed into the chamber, rotated for 10–20 seconds and allowed to incubate for 5 minutes. After this time, 150 microliters of 1 molar acetic acid containing 0.1% of Tween-20 are added to the chamber. The swab or brush is rotated for an additional 10–20 seconds. The valve structure is actuated with the swab or brush still remaining in the extraction device. The liquid contents of the extraction chamber, approximately 150–250 microliters, depending on whether a swab or brush was used, are filtered through a 1 micron filter located in the bottom of the sample receiving chamber, and are transferred to the sample pad of the test device configured to detect Chlamydia antigen. The swab or brush is removed from the device and disposed of as hazardous waste. Sample flow is initiated on the test device by capillary action and the result of the test are viewed through the test result window 10 minutes after actuating the sample receiving chamber valve.

Example 3

Method of Using Device for Detection of Genetically Modified Crops: BTK Protein To determine if corn seed, or a corn crop has been genetically modified to produce *Bacillus thuringiensis* subsp. *Kurstaki* (BtK) protein, randomly select 5 to 10 grams of corn kernels from the seed supply or from various heads of corn. Thoroughly grind the sample to ensure homogeneity. Transfer a portion of the ground sample to the sample receiving chamber of the test device until the sample fills the extraction chamber to ¾ of capacity. Add 500 microliters of normal saline. Allow this ground corn-normal saline mixture to incubate for 2 minutes. Transfer the sample receiving chamber to the test platform being careful not to spill contents. Seat the key structure of the sample receiving chamber onto the corresponding key receptor located on the test platform housing a lateral flow test strip device configured to detect BtK protein. Actuate the valve structure to allow the liquid contents to flow from the sample receiving chamber, through the 5 micron and 1 micron filters located in the bottom of the sample receiving chamber onto the sample pad of the lateral flow test strip device. This volume may vary with corn variety and the granularity of the ground corn. After 5 minutes, determine the test result through the result window. The control line preferably is present to indicate that proper sample flow has occurred.

Example 4

Method of Using Device for Food Testing: Clostridium (Liquid Samples)

To check if clostridium is present in a liquid source, first seat the key structure of the sample receiving chamber of the test device into the corresponding key receptor located on the test platform housing a lateral flow test strip device. Add 250 microliters of sample to the sample receiving chamber, followed by 50 microliters of 500 millimolar sodium phosphate buffer, pH 7.4 containing 9 grams/liter sodium chloride, 1 gram/liter bovine serum albumin and 5 milligrams/liter EDTA. Allow this solution to incubate for 30 seconds. Actuate the valve structure to allow the liquid contents to flow from the sample receiving chamber, through the 5 micron and 1 micron filters located in the bottom of the sample receiving chamber onto the sample pad of the lateral flow test device configured to detect Clostridium antigen. Approximately 250 to 300 microliters of sample transfer onto the sample pad. After 15 minutes, determine the test result through the result window. The control line is preferably present to indicate that proper flow has occurred.

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

Example 5

In Line Test Device with O-Ring Valve Actuating Mechanism

Manufacture and Construction of one Aspect of the Disclosed Test Device

The sample receiving chamber 101 made up of the male insert 102 and the female receptor 111 may be molded and formed separately from polypropylene composition. The male insert 102 with stud 103, internal incline 104, grooved ridge 105, male outlet port 106, and internal longitudinal ribs 107 may be formed as a single unit. The O-ring 108, which is separate from the male insert 102 and is seated around the male outlet port 106 of the male insert 102, can be molded and formed separately from a rubber composition. The female receptor 111 with base 112, notch 113, open groove guide 114, and female outlet port 115 may be molded and formed as a single unit from a polypropylene composition.

The test platform 120 made up of a bottom portion 121 and a top portion 131 may be molded and formed separately from a polypropylene composition. The bottom portion 121 with test strip supports 122 and snap lock mechanisms 123 may be molded and formed as a single unit from polypropylene composition. The top portion 131 with engaging structure 132, test result window 133, vent holes 134, and snap lock mechanisms 135 may be molded and formed as a single unit from polypropylene composition.

Use of one Aspect of the Test Device for Testing Disease Detection: Chlamydia

The following describes an example of a method of utilizing the integrated device of the present invention for the detection of Chlamydia. Preferably a biological specimen such as a endocervical specimen can be collected directly from a test subject using either a rayon or dacron swab with a plastic shaft or a cytobrush. The base 112 of the female receptor 111 of the sample receiving chamber 101 is attached to the engaging structure 132 of the test platform 120 housing a lateral flow test strip device. One hundred and fifty (150) microliters of 1 normal potassium hydroxide is placed into the sample receiving chamber 101 of the device. The swab or brush is placed into the chamber, rotated for 10–20 seconds and allowed to incubate for 5 minutes. After this, 150 microliters of 1 molar acetic acid containing 0.1% of Tween-20 are added to the chamber. The swab or the brush is rotated for an additional 10–20 seconds. The o-ring 108 of the valve structure protects from unintentional leakage of the content of the sample receiving chamber 101 into the test platform 120. The testing personnel actuates the o-ring 108 valve structure by rotating the grooved ridge 105 of the male insert 102 whereby the groove guide 114 slides the stud 103, and therefore the male insert 102, in a clockwise direction. This movement causes the male outlet port 106 of the male insert 102 to align with the female outlet port 115 of the female receptor 111 releasing the content of the sample receiving chamber 101 into the test platform 120. The liquid content of the sample receiving chamber, approximately 150–250microliters, depending of whether a swab or brush is used, are filtered through a 1 micron filter located in the bottom of the sample receiving chamber, and are transferred to the lateral flow test strip device configured to detect Chlamydia antigen. The internal incline 104 guides the flow of the liquid content to the aligned outlet ports of the male insert and the female receptor. The swab or brush is removed from the device and disposed of as hazardous waste. Sample flow is initiated on the test device by capillary action and the result of the test are viewed through the test result window 133 about 10 minutes after actuating the sample receiving chamber o-ring valve.

What is claimed:

1. A test device, comprising:

a) a sample receiving chamber having an open proximal end and a distal end;

said sample receiving chamber comprising a valve structure, said valve structure comprising, in combination, a male outlet port and a female receptor outlet port which engage one another to control fluid communication between the sample receiving chamber and a test platform;

b) a test platform that comprises a test element;

wherein a sample can be added to said sample receiving chamber through said open proximal end;

wherein said distal end of said sample receiving chamber engages said test platform;

wherein said sample receiving chamber is separable from said test platform;

wherein said sample receiving chamber, when separate from said test platform and containing a fluid, can engage said test platform and release said fluid into said test platform through said distal end such that said fluid contacts said test element; and wherein at least a portion of said sample can be transferred from said sample receiving chamber to said test platform by approximately or substantially aligning said male insert outlet port and said female receptor outlet port to open said valve structure.

2. The test device of claim 1, wherein said open proximal end of said receiving chamber is optionally flared.

3. The test device of claim 1, wherein said sample receiving chamber is substantially cylindrical.

4. The test device of claim 1, wherein the inside of said sample receiving chamber optionally comprises a structure to facilitate extraction of a sample.

5. The test device of claim 1, wherein said sample receiving chamber can receive a sample on a sample collection device.

6. The test device of claim 1, wherein said sample receiving chamber comprises a key structure to engage said test platform.

7. The test device of claim 1, wherein said sample receiving chamber comprises a reagent.

8. The test device of claim 1, wherein said test platform comprises a housing.

9. The test device of claim 1, wherein said test platform comprises an opening or window to observe said test element.

10. The test device of claim 1, wherein said test platform comprises a key structure to engage said distal end of said sample receiving chamber.

11. The test device of claim 1, wherein said test element comprises a test strip.

12. The test device of claim 1, wherein said test element comprises an immunological test strip.

13. The test device of claim 1, wherein said test element detects a biological moiety.

14. The test device of claim 1, wherein said test element detects a hormone, a drug, a protein, an etiological agent or a portion thereof.

15. The test device of claim 1, wherein said test element comprises a sample application zone.

16. The test device of claim 1, wherein said test element comprises a detection zone.

17. The test device of claim 1, wherein said test element comprises a solid matrix capable of supporting lateral chromatographic or capillary flow.

18. The test device of claim 1, wherein said test element is directly or indirectly in fluid communication with said sample receiving chamber.

19. The test device of claim 1, wherein said sample receiving chamber when separate from said test platform, can hold a fluid.

20. The test device of claim 1, wherein said sample receiving chamber, when separate from said test platform and containing a fluid, can engage said test platform and release a portion of said fluid into said test platform such that said portion of said fluid contacts said test element.

21. The test device of claim 1, wherein said valve structure can be repeatedly opened and closed, further wherein said valve structure being opened when said male insert outlet port and said female receptor outlet port are approximately or substantially aligned, further wherein said valve structure being closed when said male insert outlet port and said female receptor outlet port are not approximately or substantially aligned.

22. The test device of claim 1, wherein said valve structure can optionally lock in an open or a closed position.

23. The test device of claim 1, wherein said valve structure further comprises a male insert and a female receptor, wherein said male insert comprises said male insert outlet port and said female receptor comprises said female receptor outlet port, wherein said approximately or substantially aligning said male insert outlet port and said female receptor outlet port is performed by altering a position of either said male insert or said female receptor.

24. The test device of claim 23, further comprising a seal structure positioned between said male insert and said female receptor, wherein said seal structure prevents or reduces sample leakage from said sample receiving chamber when said valve structure is in a closed position.

25. The test device of claim 24, wherein said seal structure is an O-ring.

26. The test device of claim 1, further comprising one or more filters to reduce particulate matter contacting said test element.

27. The test device of claim 1, further comprising a reagent.

28. The test device of claim 1, further comprising instructions.

29. The test device of claim 1, wherein said sample receiving chamber is substantially perpendicular to said test platform when said sample receiving chamber and said test platform are operably engaged.

30. A method of detecting an analyte in a sample, comprising:

providing a sample suspected of comprising an analyte;

contacting said sample with the test device of claim 1;

releasing said analyte from said sample receiving chamber; and detecting said analyte in said sample.

31. The method of claim 30, wherein said sample is a biological sample.

32. The method of claim 30, wherein said sample is provided on a sample collection device.

33. The method of claim 30, wherein said sample is provided on a swab.

34. The method of claim 30, wherein said sample is extracted in said sample receiving chamber.

35. The method of claim 30, wherein said sample is extracted in said sample receiving chamber using an extraction solution.

36. The method of claim 30, wherein said analtye is a biological or chemical moiety.

37. The method of claim 30, wherein said analyte is extracted from said sample.

38. The method of claim 30, wherein said analtye is an etiological agent, derived from an etiological agent or extracted from an etiological agent.

39. The method of claim 30, wherein said sample is placed in said sample receiving chamber, optionally with a reagent; wherein when said reagent is present, said reagent can be added to said sample receiving chamber before or after said sample is placed therein.

40. The method of claim 39, wherein said sample receiving chamber is optionally engaged with said test platform when said sample is contacted with said test device.

41. The method of claim 39, wherein said sample is contacted with said sample receiving chamber with a reagent.

42. The method of claim 39, wherein said sample with a reagent in said sample receiving chamber are allowed to mix or incubate in said sample receiving chamber.

43. The method of claim 39, wherein when said sample receiving chamber and said test platform are separate, a sample is provided in said sample receiving chamber with a reagent and said sample receiving chamber is then operably engaged with said test platform.

44. The method of claim 39, wherein when said sample receiving chamber and said test platform are separate, a sample is provided in said sample receiving chamber without a reagent and said sample receiving chamber is then operably engaged with said test platform.

45. The method of claim 44, wherein after said sample receiving chamber is operably engaged with said test platform, a reagent is added.

46. The method of claim 39, wherein sample is allowed to flow through a filter prior to contacting said test element.

47. The method of claim 39, wherein said valve structure actuates or modulates fluid flow between said sample receiving chamber and said test platform.

* * * * *